United States Patent
Vaughn et al.

(10) Patent No.: US 7,090,081 B2
(45) Date of Patent: Aug. 15, 2006

(54) SELECTIVELY REMOVING UNDESIRABLY SIZED CATALYST PARTICLES FROM A REACTION SYSTEM

(75) Inventors: Stephen Neil Vaughn, Kingwood, TX (US); Kenneth Ray Clem, Humble, TX (US); Keith Holroyd Kuechler, Friendswood, TX (US); James R. Lattner, Seabrook, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 252 days.

(21) Appl. No.: 10/656,673

(22) Filed: Sep. 5, 2003

(65) Prior Publication Data

US 2005/0067326 A1    Mar. 31, 2005

(51) Int. Cl.
*B07B 7/00*    (2006.01)
*C07C 1/00*    (2006.01)

(52) U.S. Cl. .................................. 209/154; 585/639
(58) Field of Classification Search ............... 209/132, 209/710, 715, 725, 235, 238, 716, 145, 154; 585/639, 640; 502/21
See application file for complete search history.

(56) References Cited

U.S. PATENT DOCUMENTS

| | | | | |
|---|---|---|---|---|
| 2,573,559 A | | 10/1951 | Friedman ................. 260/449.6 |
| 2,631,981 A | | 3/1953 | Watson et al. ................. 252/17 |
| 3,785,962 A | * | 1/1974 | Conner et al. ............... 208/164 |
| 4,279,743 A | * | 7/1981 | Miller ......................... 209/731 |
| 4,302,565 A | * | 11/1981 | Goeke et al. ................. 526/88 |
| 4,666,586 A | * | 5/1987 | Farnsworth ................. 208/161 |
| 4,810,264 A | * | 3/1989 | Dewitz ......................... 48/210 |
| 5,177,279 A | | 1/1993 | Harandi ...................... 585/312 |
| 5,393,412 A | | 2/1995 | Hettinger .................... 208/120 |
| 5,518,695 A | | 5/1996 | Goodspeed et al. ........ 422/144 |
| 5,636,747 A | | 6/1997 | Hettinger, Jr. et al. ...... 209/213 |
| 5,744,680 A | * | 4/1998 | Mulvaney et al. .......... 585/640 |
| 5,746,321 A | | 5/1998 | Hettinger, Jr. et al. ...... 209/233 |
| 6,023,005 A | | 2/2000 | Lattner et al. |
| 6,580,010 B1 | * | 6/2003 | Searle ........................ 585/809 |

FOREIGN PATENT DOCUMENTS

WO    WO 02/05950    1/2002

OTHER PUBLICATIONS

Fisher-Klosterman, Inc, Product Bulletin for EX Series Aerodynamic Particle Classifier, Revised Aug. 2000.*
Geldart, D., "The Effect of Particle Size and Particle Size Distribution on the Behaviour of Gas-Fluidized Beds," Powder Technology, 6, (1972), p. 201-215.
Hiltunene, J., et al., "NExCC-Novel Short Contact Time Catalyst Cracking Technology," Fluid Catalytic Cracking V: Materials and Technological Innovations, Sec. 5, Occelli/O'Connor (eds.), Elsevier 2001.

(Continued)

*Primary Examiner*—Joseph Rodriguez

(57) ABSTRACT

The present invention provides various processes for selectively removing undesirably sized catalyst particles from a reaction system. In one embodiment, a plurality of catalyst particles, having a first median particle diameter, is withdrawn from the reaction system and is directed to a separation unit such as a counter flow cyclone separator. In the separation unit, the particles are separated into a small catalyst stream and a large catalyst stream, the small catalyst stream having a second median particle diameter less than the first median particle diameter, and the large catalyst stream having a third median particle diameter greater than the first median particle diameter. At least a portion of the small or large catalyst stream is then directed back to the reaction system in order to maintain a desirable particle size distribution therein.

14 Claims, 3 Drawing Sheets

OTHER PUBLICATIONS

Perry et al., Chemical Engineer's Handbook, 5th Ed., 1973, pp. 21-46 to 21-50.
U.S. Appl. No. 10/170,939, filed Jun. 13, 2002, Xu et al.
U.S. Appl. No. 09/887,860, filed Jun. 22, 2001, Coute et al.
U.S. Appl. No. 10/218,728, filed Aug. 14, 2002, Vaughn et al.
Fisher-Klosterman, Inc., Aerodynamic Classifier, classifierdiag. htmclassifierdiag.htm, date unknown.

* cited by examiner

SELECTIVELY REMOVING UNDESIRABLY SIZED CATALYST PARTICLES FROM A REACTION SYSTEM

FIELD OF THE INVENTION

The present invention relates to processes for selectively removing particles from a reaction system. More particularly, the present invention relates to selectively removing undesirably large and/or small catalyst particles from an oxygenate to olefin reaction system in order to maintain a desirable catalyst particle size distribution therein.

BACKGROUND OF THE INVENTION

Light olefins, defined herein as ethylene and propylene, serve as feeds for the production of numerous chemicals. Olefins traditionally are produced by petroleum cracking. Because of the limited supply and/or the high cost of petroleum sources, the cost of producing olefins from petroleum sources has increased steadily.

Oxygenates such as alcohols, particularly methanol, dimethyl ether, and ethanol, are alternative feedstocks for the production of light olefins. Alcohols may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for olefin production.

In an oxygenate to olefin (OTO) reaction system, an oxygenate in an oxygenate-containing feedstock contacts a molecular sieve catalyst composition under conditions effective to convert at least a portion of the oxygenate to light olefins, which are yielded from the reaction system in a reaction effluent. As the feedstock contacts the molecular sieve catalyst compositions at high weight hourly space velocities and under extreme temperature and pressure conditions, a portion of the catalyst compositions can shear or break away, e.g., attrite, to form one or more smaller catalyst attrition particles. Some catalyst attrition particles are very small in size and are referred to as catalyst fines. Due to their relatively high surface area to mass ratios, a portion of the catalyst fines in the reaction system may become undesirably entrained with the reaction effluent and exit the reaction system therewith. Conversely, due to their relatively low surface area to mass ratios, larger particles tend to be selectively retained in OTO reaction systems. The selective retention of larger particles is particularly a problem for highly attrition resistant particles.

The build up of large catalyst particles in an OTO reaction system produces two undesirable effects. First, in a large particle rich reaction system, the circulating fluid bed will not operate as well, particularly with regard to circulation of catalyst within the standpipes. Second, the large particles that are selectively retained in the reaction system will tend to lose their effectiveness, e.g., activity and selectivity, with time. That is, the build up of large particles in the reaction system is undesirable because the larger particles will tend to decrease the overall effectiveness of the collection of catalyst particles contained in the reaction system.

One conventional technique for removing undesirably-sized catalyst particles includes non-selectively removing a fraction of all of the catalyst particles in the reaction system to make room for the addition of fresh catalyst. This technique for removing undesirably-sized catalyst particles is inefficient, however, because a significant portion of the desirably-sized catalyst particles are removed from the reaction system with the undesirably-sized catalyst particles.

U.S. Pat. No. 5,746,321 to Hettinger, Jr. et al. discloses the combination of a magnetic separator, a catalyst classifier, and/or a catalyst attriter, which wears off the outer layers of catalyst, yields more active catalyst of lower metal content with closer control of average particles size, and narrows particle size distribution providing improved fluidization properties and better activity and selectivity. The process is especially useful when processing high metal-containing feedstocks.

U.S. Pat. No. 2,573,559 to Friedman discloses replacing a bed of fluidized catalyst, which has become reduced in activity during use, with fresh fluidized catalyst, the average particle size of both catalysts being in the range of 40–400 mesh. The average size of the fresh catalyst differs from that of the partially spent catalyst by at least 10-mesh size and preferably 25 mesh. The fresh catalyst is introduced into the reactor under conditions such that the reaction temperature is not substantially increased, and at the same time catalyst is withdrawn from the reactor at a portion below the top level of the bed. The catalyst withdrawn is separated by particle size into fresh catalyst, which is returned to the reactor, and deactivated catalyst, which is regenerated. According to the '559 patent, the complete replacement of catalyst can be accomplished under normal operating conditions in from 20 to 48 hours.

In certain reaction systems, the removal of small catalyst particles may be desired. For example, if a reaction system implements catalyst compositions having low attrition resistance, then the catalyst compositions may, depending on reaction conditions, readily attrite and form catalyst fines. The increase in the proportion of catalyst fines in the reaction system will decrease the median particle diameter of the entire catalyst population in the reaction system, which may undesirably impact the fluidization characteristics within the reaction system. Undesirably high levels of fines may make it difficult to maintain desired fluid bed densities and thus adversely affect the reaction rates associated with the reaction zone. As a result, it may be desired to selectively remove small catalyst particles, e.g., catalyst fines, from a reaction system in order to maintain a desired particle size distribution in the reaction system.

In view of the importance of maintaining desirably-sized catalyst particles in reaction systems, particularly in OTO reaction systems, improved processes are sought for selectively removing undesirably-sized catalyst particles from OTO reaction systems. More specifically, improved processes are sought that can maintain a desirable catalyst particle size distribution in an OTO reaction system and thereby provide desirable fluidization and catalytic activity characteristics.

SUMMARY OF THE INVENTION

This invention provides novel processes and systems for selectively removing catalyst particles, based on their size, from an OTO reaction system. By selectively removing undesirably-sized catalyst particles from the OTO reaction system, desirable fluidization and catalytic activity characteristics can be realized therein.

In one embodiment, the invention is to a process for selectively removing large catalyst particles from a reaction system, wherein the reaction system comprises a reaction zone, a disengaging zone, optionally a catalyst regenerator, optionally a catalyst cooler and optionally a catalyst stripper. In the process, a plurality of catalyst particles is fed into the reaction zone. The plurality of catalyst particles contacts a feedstock in the reaction zone under conditions effective to convert at least a portion of the feedstock to product. A portion of the plurality of catalyst particles, having a first median particle diameter, is directed from the reaction system to a separation unit. The portion of the plurality of catalyst particles is separated in the separation unit into a small catalyst stream and a large catalyst stream, wherein the small catalyst stream has a second median particle diameter less than the first median particle diameter. The large catalyst stream has a third median particle diameter greater than the first median particle diameter. At least a portion of the small catalyst stream is directed to the reaction system.

The separation unit optionally is selected from the group consisting of: a cyclone separator, a settling vessel, a screen and an air classifier. In one embodiment, the separating step comprises contacting the portion of the plurality of catalyst particles with a turbulizing stream under conditions effective to form the small catalyst stream and the large catalyst stream. In one embodiment, the separation device comprises a tunable cyclone.

In another embodiment, the invention is also directed to a process for selectively removing large catalyst particles from a reaction system, wherein the reaction system comprises a reaction zone, a disengaging zone, optionally a catalyst regenerator, optionally a catalyst cooler and optionally a catalyst stripper. This process includes a step of feeding a plurality of catalyst particles into the reaction zone. The plurality of catalyst particles contacts a feedstock in the reaction zone under conditions effective to convert at least a portion of the feedstock to product, wherein the plurality of catalyst particles comprises catalyst fines and catalyst non-fines. The product and the plurality of catalyst particles is then directed to the disengaging zone. An effluent stream is yielded from the disengaging zone, wherein the effluent stream comprises at least a majority of the product and at least a portion of the catalyst fines. At least a majority of the catalyst non-fines are directed from the disengaging zone to the reaction zone, and a portion of the plurality of catalyst particles is directed from the reaction system to a separation zone, wherein the portion has a first median particle diameter. The portion is separated in the separation zone into a small catalyst stream and a large catalyst stream, wherein the small catalyst stream has a second median particle diameter less than the first median particle diameter. At least a portion of the small catalyst stream is directed to the reaction system.

In one embodiment, the process includes a step of providing a first plurality of catalyst particles in a reaction zone, wherein the first plurality of catalyst particles has a first median particle diameter, and wherein the first plurality of catalyst particles comprises catalyst fines. The first plurality of catalyst particles contacts a feedstock in the reaction zone under conditions effective to convert at least a portion of the feedstock to product. The first plurality of catalyst particles is directed from the reaction zone to a disengaging zone. A portion of the catalyst fines are removed from the disengaging zone under conditions effective to form a second plurality of catalyst particles in the disengaging zone, wherein the second plurality of catalyst particles has a second median particle diameter greater than the first median particle diameter. A portion of the second plurality of catalyst particles is directed from the reaction zone or the disengaging zone to a separation zone. The portion of the second plurality of catalyst particles is separated into a small catalyst stream and a large catalyst stream, wherein the small catalyst stream has a third median particle diameter less than the second median particle diameter. At least a portion of the small catalyst stream is directed to the reaction system, e.g., to either the reaction zone, the disengaging zone, or to another part of the reaction system.

In another embodiment, the invention is directed to a process for selectively removing small catalyst particles from a reaction system. The reaction system comprises a reaction zone, a disengaging zone, optionally a catalyst regenerator, optionally a catalyst cooler and optionally a catalyst stripper. The process includes a step of feeding a plurality of catalyst particles into the reaction zone. The plurality of catalyst particles contacts a feedstock in the reaction zone under conditions effective to convert at least a portion of the feedstock to product. A portion of the plurality of catalyst particles is directed from the reaction system to a separation unit, wherein the portion of the plurality of catalyst particles has a first median particle diameter. The portion of the plurality of catalyst particles is separated in the separation unit into a small catalyst stream and a large catalyst stream, wherein the small catalyst stream has a second median particle diameter, and the large catalyst stream has a third median particle diameter greater than the first median particle diameter. At least a portion of the large catalyst stream is directed to the reaction system.

In another embodiment, the invention is directed to a process for maintaining a catalyst particle size distribution in a reaction system. The process comprises directing a first plurality of catalyst particles having a first median particle diameter from the reaction system to a first separation zone. The first plurality of catalyst particles is separated into a first small catalyst stream and a first large catalyst stream, wherein the first small catalyst stream has a second median particle diameter less than the first median particle diameter, and wherein the first large catalyst stream has a third median particle diameter greater than the first median particle diameter. At least a portion of the first small catalyst stream is separated into a second small catalyst stream and a second large catalyst stream, wherein the second small catalyst stream has a fourth median particle diameter less than the second median particle diameter, and wherein the second large catalyst stream has a fifth median particle diameter greater than the second median particle diameter. At least a portion of the second large catalyst stream is directed back to the reaction system.

In another embodiment, the invention is directed to a process for maintaining a catalyst particle size distribution in a reaction system. The process comprises directing a first plurality of catalyst particles having a first median particle diameter from the reaction system to a first separation zone. The first plurality of catalyst particles is separated into a first small catalyst stream and a first large catalyst stream, wherein the first small catalyst stream has a second median particle diameter less than the first median particle diameter, and wherein the first large catalyst stream has a third median particle diameter greater than the first median particle diameter. At least a portion of the first large catalyst stream is separated into a second small catalyst stream and a second large catalyst stream, wherein the second small catalyst stream has a fourth median particle diameter less than the third median particle diameter, and wherein the second large catalyst stream has a fifth median particle diameter greater than the third median particle diameter. At least a portion of the second small catalyst stream is directed back to the reaction system.

BRIEF DESCRIPTION OF THE DRAWINGS

This invention will be better understood by reference to the detailed description of the invention when taken together with the attached drawings, wherein.

DETAILED DESCRIPTION OF THE INVENTION

Introduction

Figure 1:
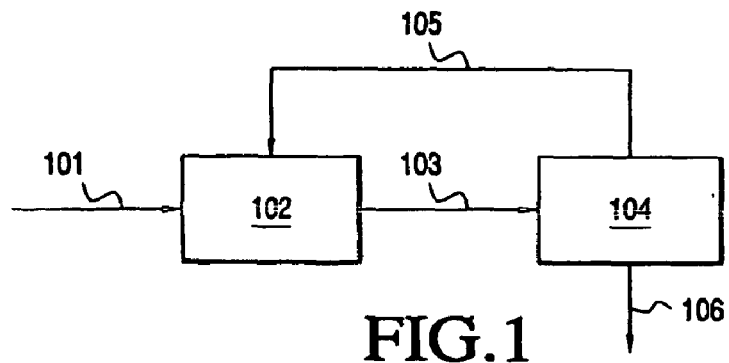
FIG. 1 illustrates one embodiment of the present invention.

The present invention provides various processes for selectively removing undesirably large and/or small catalyst particles from a reaction system. In one embodiment, the invention is to a process for selectively removing large catalyst particles from a reaction system. As used herein, "reaction system" means a system comprising a reaction zone, a disengaging zone, optionally a catalyst regenerator, optionally a catalyst cooler and optionally a catalyst stripper. In the process, a plurality of catalyst particles is fed into the reaction zone. The plurality of catalyst particles contacts a feedstock in the reaction zone under conditions effective to convert at least a portion of the feedstock to product. A portion of the plurality of catalyst particles, having a first median particle diameter, is directed from the reaction system to a separation unit. The portion of the plurality of catalyst particles is separated in the separation unit into a small catalyst stream and a large catalyst stream, wherein the small catalyst stream has a second median particle diameter less than the first median particle diameter. The large catalyst stream has a third median particle diameter greater than the first median particle diameter. At least a portion of the small catalyst stream is directed to the reaction system. Additionally or alternatively, at least a portion of the large catalyst stream is directed back to the reaction system. According to the present invention, a desirable particle size distribution can be maintained in the reaction system.

In a preferred embodiment, the separation unit comprises a tunable cyclone into which a turbulizing stream is introduced. As used herein, a "turbulizing stream" is a flow of gas which is introduced into a cyclone separator and which at least partially disrupts the downward flow of larger catalyst particles contained in the cyclone separator. In effect, the turbulizing stream reduces the separation efficiency of a cyclone separator in a controllable way so that the extent of particle separation can be adjusted. Specifically, the turbulizing stream contacts an outer cyclone (containing larger catalyst particles) formed in the cyclone separator under conditions effective to control the cut between the small catalyst stream and the large catalyst stream.

Processes for Selectively Removing Catalyst Particles from a Reaction System

In a preferred embodiment of the present invention, a portion of the catalyst particles in a reaction system is removed therefrom and is directed to a separation unit for selectively separating larger catalyst particles from smaller catalyst particles. Preferably, the removed portion of catalyst particles is an aliquot portion of catalyst particles. By aliquot, it is meant that the portion of catalyst particles removed from the reaction system for separation of large catalyst particles from small catalyst particles is substantially representative of the entire catalyst population within the reaction system. It is contemplated, however, that the portion of catalyst particles withdrawn from the reaction system may be a non-aliquot portion. For example, if the portion of catalyst particles withdrawn from the reaction system is taken from the bottom of a reaction unit, that portion may contain a slightly greater median particle diameter than the median particle diameter of the entire population of catalyst particles in the reaction system due to catalyst settling in the reaction unit.

As used herein, a "median particle diameter" is the d50 value for a specified plurality of particles. The dx particle size for purposes of this patent specification and appended claims means that x percent by volume of a specified plurality of particles have a particle diameter no greater than the dx value. For the purposes of this definition, the particle size distribution (PSD) used to define the dx value is measured using well known laser scattering techniques using a Microtrac Model S3000 Particle Size Analyzer from Microtrac, Inc. (Largo, Fla.). "Particle diameter" as used herein means the diameter of a specified spherical particle or the equivalent diameter of non-spherical particles as measured by laser scattering using a Microtrac Model S3000 Particle Size Analyzer.

As indicated above, according to the present invention a portion of catalyst particles from a reaction system is directed to a separation unit. Optionally, the portion of catalyst particles is directed to the separation unit from a reaction zone, a disengaging zone, catalyst regenerator, a stripping unit, a catalyst cooler, or a combination of these units. The portion of catalyst particles has a first median particle diameter. In the separation unit, the portion of catalyst particles is separated into a small catalyst stream and a large catalyst stream. The small catalyst stream has a second median particle diameter less than the first median particle diameter, and the large catalyst stream has a third median particle diameter greater than the first median particle diameter. In one embodiment, at least a portion of the small catalyst stream is directed, ultimately, back to the reaction system. Additionally or alternatively, at least a portion of the large catalyst stream is directed, ultimately, back to the reaction system.

Optionally, the first median particle diameter is from 60 to 120, from 65 to 100 or from 65 to 85 microns. Optionally, the second median particle diameter is less than 120 microns, no greater than or less than about 100 microns, or no greater than about 80 microns. Optionally, the third median particle diameter is at least about 100 microns, at least about 120 microns, at least about 150 microns, or at least about 200 microns.

As disclosed in more detail below, the preferred reaction system is an oxygenate to olefin (OTO) reaction system. The OTO reaction system preferably comprises a reaction unit (which defines a reaction zone), a disengaging unit (which defines a disengaging zone), a catalyst stripper, a catalyst regenerator, a catalyst cooler, and conduit lines connecting these units. Optionally, the portion of the plurality of catalyst particles that is directed to the separation unit is withdrawn from one or more of the reaction unit, the disengaging unit, the catalyst stripper, the catalyst regenerator, the catalyst cooler and/or the conduits connecting these units.

Conversely, the desirably-sized catalyst stream from the separation unit or units, or a portion thereof, optionally is directed to one or more of the reaction unit, the disengaging unit, the catalyst stripper, the catalyst regenerator, the catalyst cooler, and/or one or more of the conduit lines connecting these units. In a particularly preferred embodiment, illustrated and discussed in more detail below with reference to FIG. 5, the portion of the plurality of catalyst particles that is directed to the separation unit is withdrawn from a conduit line that transports catalyst from a catalyst regenerator to the reaction unit.

In one embodiment of the present invention, the reaction unit is in fluid communication with a disengaging unit, which defines a disengaging zone and which is provided to separate catalyst particles from products of the reaction process. The catalyst particles that are received in the disengaging zone preferably comprise catalyst fines, catalyst coarses, catalyst nonfines, and catalyst noncoarses.

"Catalyst fines" are defined herein as a collection of formulated catalyst composition particles having a median particle diameter no greater than 20 microns. As used herein, "catalyst nonfines" are defined herein as a collection of formulated catalyst composition particles having a median particle diameter greater than 20 microns. "Catalyst coarses" are defined herein as a collection of formulated catalyst composition particles having a median particle diameter of at least 120 microns. As used herein, "catalyst noncoarses" are defined herein as a collection of formulated catalyst composition particles having a median particle diameter of less than 120 microns. A "heart cut" is defined herein as a collection of formulated catalyst composition particles having a median particle diameter greater than 20 microns and less than 120 microns. As used herein, the terms "large" and "small," when referring to a population of catalyst particles, are relative and refer to a median particle diameter of a plurality of catalyst particles. Thus, a "large" catalyst stream may contain some small catalyst particles, e.g., catalyst fines. Additionally, the size of particles contained in a "large catalyst stream" and a "small catalyst stream" will vary depending on the particle size distribution of a parent stream the is separated to produce the large and small catalyst streams. Thus, a large catalyst stream might not contain any catalyst coarses, if the parent stream from which it was derived did not contain catalyst coarses. Similarly, a small catalyst stream might not contain any catalyst fines, if the parent stream from which it was derived did not contain catalyst fines.

In one embodiment, the present invention is directed to a process for selectively removing large catalyst particles from a reaction system, which comprises a reaction zone, a disengaging zone, optionally a catalyst regenerator, optionally a catalyst cooler and optionally a catalyst stripper. This process includes a step of feeding a plurality of catalyst particles into the reaction zone. The plurality of catalyst particles contacts a feedstock in the reaction zone under conditions effective to convert at least a portion of the feedstock to product, wherein the plurality of catalyst particles comprises catalyst fines and catalyst non-fines. Preferably, the feedstock comprises an oxygenate, preferably methanol, and the product comprises light olefins, e.g., ethylene and propylene. The product and the plurality of catalyst particles is then directed to the disengaging zone. The disengaging zone is in fluid communication with the reaction zone. An effluent stream, which comprises at least a majority of the product and at least a portion of the catalyst fines, is yielded from the disengaging zone. At least a majority of the catalyst non-fines are directed from the disengaging zone to the reaction zone, and a portion of the plurality of catalyst particles is directed from the reaction system (e.g., from one or more of the reaction zone, the disengaging zone, the catalyst regenerator, the catalyst cooler and/or the catalyst stripper) to a separation zone, wherein the portion has a first median particle diameter. The portion is separated in the separation zone into a small catalyst stream and a large catalyst stream, wherein the small catalyst stream has a second median particle diameter less than the first median particle diameter. The large catalyst stream has a third median particle diameter greater than the first median particle diameter.

In this embodiment of the present invention, the separation zone optionally comprises a separation unit selected from the group consisting of: cyclone separators, settling vessels, screens, and air classifiers. Preferably, the separation zone comprises a counter flow cyclone separator, discussed below. Finally, at least a portion of the small catalyst stream is directed back to the reaction system, e.g., to one or more of the reaction zone, the disengaging zone, the catalyst regenerator, the catalyst cooler and/or the catalyst stripper. Additionally or alternatively, at least a portion of the large catalyst stream is directed back to the reaction system.

In each of these embodiments, the disposition of the undesirably-sized catalyst stream (e.g., undesirably large or undesirably small) may vary widely. In one embodiment, the undesirably-sized catalyst stream or a portion thereof is disposed of. Additionally or alternatively, the undesirably-sized catalyst stream, or a portion thereof, is directed to a catalyst synthesis system, wherein the undesirably-sized catalyst stream or a portion thereof is formulated into a new molecular sieve catalyst composition. Additionally or alternatively, the undesirably-sized catalyst stream, or a portion thereof, may be physically crushed to provide, for example, a source of more desirably sized particles.

The flow rate of catalyst that is directed to the separation unit from the reaction system may vary widely. In a preferred embodiment of the present invention, the flow rate of catalyst that is directed from the reaction system to the separation unit is from about 0.01 weight percent to about 50 weight percent of the catalyst inventory/day, more preferably from about 0.05 weight percent to about 25 weight percent of the catalyst inventory/day, and most preferably from about 0.1 weight percent to about 10 weight percent of the catalyst inventory/day.

In one embodiment, the process of the present invention provides for the ability to maintain a desired particle size distribution within a reaction system although a portion of the catalyst fines in the reaction system may exit the reaction system with the product effluent. In this embodiment, the present invention provides a process for selectively removing large catalyst particles from the reaction system.

The process includes a step of providing a first plurality of catalyst particles in a reaction zone. The first plurality of catalyst particles has a first median particle diameter and comprises catalyst fines. The first plurality of catalyst particles contacts a feedstock in the reaction zone under conditions effective to convert at least a portion of the feedstock to product. The first plurality of catalyst particles is then directed from the reaction zone to a disengaging zone. A portion of the catalyst fines are removed from the disengaging zone under conditions effective to form a second plurality of catalyst particles in the disengaging zone. The second plurality of catalyst particles has a second median particle diameter greater than the first median particle diameter. A portion of the second plurality of catalyst particles is directed from the reaction zone or the disengaging zone to a separation zone. In the separation zone, the portion of the second plurality of catalyst particles is separated into a small catalyst stream and a large catalyst stream. The small catalyst stream has a third median particle diameter less than the second median particle diameter. The large catalyst stream has a fourth median particle diameter, which is greater than the second median particle diameter. Finally, at least a portion of the small catalyst stream is directed to the reaction system.

This embodiment optionally further comprises a step of monitoring the second median diameter. The monitoring preferably is performed by a laser scattering particle size analyzer such as a Microtrac Model S3000 Particle Size Analyzer from Microtrac, Inc. (Largo, Fla.). The monitoring may occur either online or offline. In this embodiment, the step of directing a portion of the second plurality of catalyst particles to the separation zone preferably is responsive to a determination in the monitoring step that the second median particle diameter has exceeded a predetermined limit. The predetermined limit may vary widely, but preferably is greater than 120 microns, between about 100 and about 120 microns, or between about 90 and about 100 microns. Optionally, the monitoring is performed by a laser scattering particle size analyzer, a Coulter counter, device for determining rate of sedimentation, or a mechanical screening device.

The present invention is also directed to processes for selectively removing small catalyst particles from a reaction system, which comprises a reaction zone, a disengaging zone, optionally a catalyst regenerator, optionally a catalyst cooler and optionally a catalyst stripper. In one embodiment, the process includes a step of feeding a plurality of catalyst particles into the reaction zone. The plurality of catalyst particles contacts a feedstock in the reaction zone under conditions effective to convert at least a portion of the feedstock to product. A portion of the plurality of catalyst particles is directed from the reaction system to a separation unit, wherein the portion of the plurality of catalyst particles has a first median particle diameter. The portion of the plurality of catalyst particles is separated in the separation unit into a small catalyst stream and a large catalyst stream, wherein the small catalyst stream has a second median particle diameter, and the large catalyst stream has a third median particle diameter greater than the first median particle diameter. At least a portion of the large catalyst stream is directed to the reaction system.

This inventive process for selectively removing small catalyst particles from a reaction system is ideally suited for a reaction system that implements catalyst particles having very low attrition resistance. That is, in a reaction system that implements catalyst particles having low attrition resistance, the catalyst particles will tend to attrite at a higher rate than in a reaction system that implements highly attrition resistant catalyst particles. As a result, the median particle diameter of a reaction system that implements catalyst particles having a lower attrition resistance will decrease as attrition occurs. In order to maintain the desired particle size distribution in such a reaction system, in one embodiment, at least a portion of the catalyst fines are removed therefrom thereby maintaining the desired particle size distribution.

In another embodiment, the present invention is directed to a process for maintaining a catalyst particle size distribution in a reaction system, wherein the process comprises a separation of catalyst particles in a plurality, preferably two, separation steps. Specifically, a first plurality of catalyst particles having a first median particle diameter is directed from the reaction system to a first separation zone. The first plurality of catalyst particles is separated in the first separation zone into a first small catalyst stream and a first large catalyst stream. The first small catalyst stream has a second median particle diameter less than the first median particle diameter, and the first large catalyst stream has a third median particle diameter greater than the first median particle diameter. At least a portion of the first small catalyst stream is separated into a second small catalyst stream and a second large catalyst stream. The second small catalyst stream has a fourth median particle diameter less than the second median particle diameter, and the second large catalyst stream has a fifth median particle diameter greater than the second median particle diameter. At least a portion of the second large catalyst stream is directed back to the reaction system. Optionally, either or both of the above described separation steps occurs in a separation unit selected from the group consisting of a cyclone separator, a settling device, a screen and an air classifier. Preferably however, at least one, preferably both, separation steps occur in a counter flow cyclone separator.

In an alternative embodiment of the present invention, undesirably small catalyst particles, e.g., catalyst fines, are removed in a first separation step, followed by separation of undesirably large catalyst particles, e.g., catalyst coarses, in a second separation step. In this embodiment, a first plurality of catalyst particles having a first median particle diameter is directed from the reaction system to a first separation zone. The first plurality of catalyst particles is separated into a first small catalyst stream and a first large catalyst stream. The first small catalyst stream has a second median particle diameter less than the first median particle diameter, and the first large catalyst stream has a third median particle diameter greater than the first median particle diameter. In the second separation step, at least a portion of the first large catalyst stream is separated into a second small catalyst stream and a second large catalyst stream. The second small catalyst stream has a fourth median particle diameter less than the third median particle diameter, and the second large catalyst stream has a fifth median particle diameter greater than the third median particle diameter. At least a portion of the second small catalyst stream is directed back to the reaction system.

Figure 2:
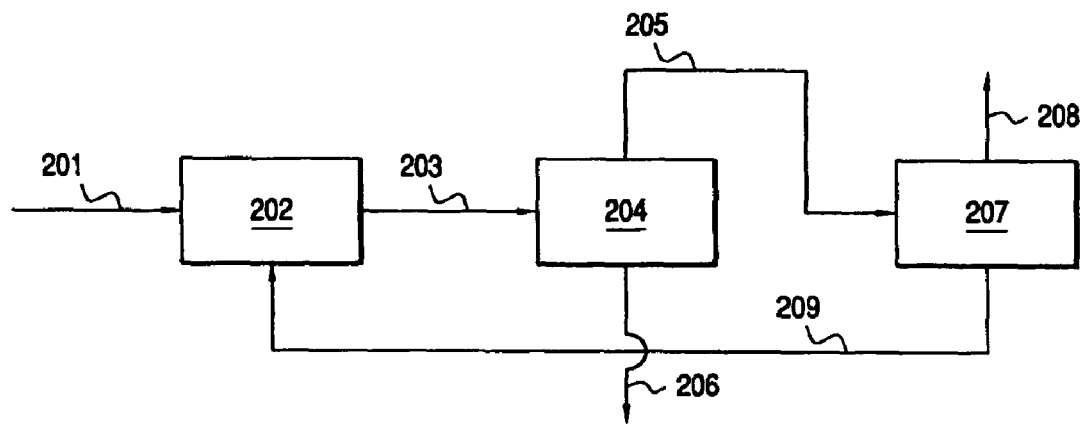
FIG. 2 illustrates another embodiment of the present invention.
Figure 3:
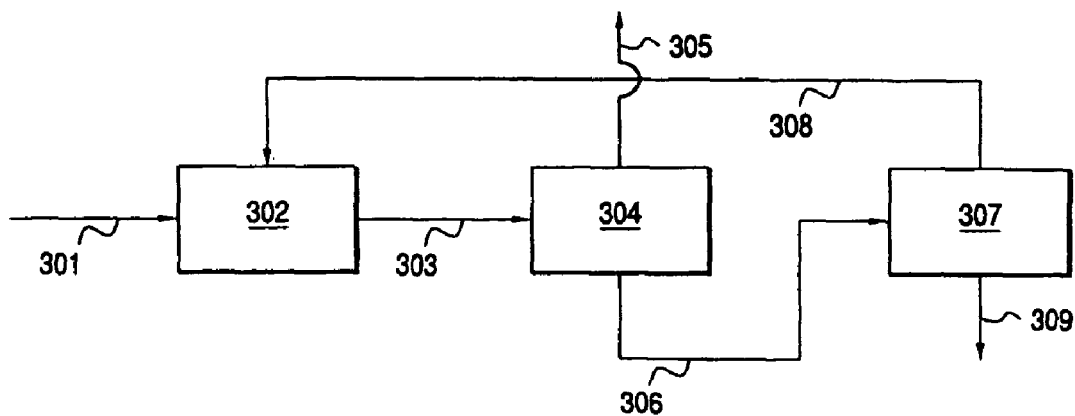
FIG. 3 illustrates another embodiment of the present invention.

FIGS. 1–3 illustrate three non-limiting exemplary embodiments of the present invention. FIG. 1, for example, illustrates an embodiment of the present invention wherein large catalyst particles are selectively separated from smaller catalyst particles, which are recycled back to the reaction system. Specifically, a feedstock 101, which preferably contains an oxygenate such as methanol or ethanol, is directed to a reaction system 102. In the reaction system 102, a first portion of catalyst particles contacts the feedstock under conditions effective to convert at least a portion of the feedstock 101 to product, which exits the reaction system 102 in a reaction effluent stream, not shown. The reaction system 102 includes a reaction unit and optionally one or more of the following units: a disengaging unit, a catalyst stripper, a catalyst regenerator, a catalyst cooler, and/or conduit lines transferring catalyst particles between these units.

A second portion of catalyst particles 103 (e.g., a portion of the first portion of catalyst particles) is withdrawn from the reaction system 102 and is directed to separation system 104. Separation system 104 comprises one or more separation units, which are adapted to separate large catalyst particles from smaller catalyst particles. As shown, separation system 104 selectively separates the second portion of catalyst particles 103 into a small catalyst stream 105 and a large catalyst stream 106. Small catalyst stream 105 has a median particle diameter less than the median particle diameter of the second portion of catalyst particles 103, and large catalyst stream 106 has a median particle diameter greater than the median particle diameter of the second portion of catalyst particles 103. As shown, small catalyst stream 105 is returned to reaction system 102 to catalyze further conversion of feedstock 101 to product. Large catalyst stream 106 optionally is recycled to a catalyst formulating facility or disposed of. In another embodiment, not shown, large catalyst stream 106 is returned to reaction system 102 to catalyze further conversion of feedstock 101 to product. In this embodiment, small catalyst stream 105 optionally is recycled to a catalyst formulating facility or disposed of.

FIG. 2 illustrates another embodiment of the present invention, wherein small and large catalyst particles are selectively removed from the reaction system to form a population of desirably-sized catalyst particles, which are directed back to the reaction system. Specifically, a feedstock 201, which preferably contains an oxygenate such as methanol or ethanol, is directed to a reaction system 202. In the reaction system 202, a first portion of catalyst particles contacts the feedstock under conditions effective to convert at least a portion of the feedstock 201 to product, which exits the reaction system 202 in a reaction effluent stream, not shown. The reaction system 202 includes a reaction unit and optionally one or more of the following units: a disengaging unit, a catalyst stripper, a catalyst regenerator, a catalyst cooler, and/or conduit lines transferring catalyst particles between these units.

A second portion of catalyst particles 203 (e.g., a portion of the first portion of catalyst particles) is withdrawn from the reaction system 202 and is directed to a first separation system 204. First separation system 204 comprises one or more separation units, which are adapted to separate large catalyst particles from smaller catalyst particles. As shown, first separation system 204 selectively separates the second portion of catalyst particles 203 into a first small catalyst stream 205 and a first large catalyst stream 206. First small catalyst stream 205 has a median particle diameter less than the median particle diameter of the second portion of catalyst particles 203, and first large catalyst stream 206 has a median particle diameter greater than the median particle diameter of the second portion of catalyst particles 203.

First small catalyst stream 205 is directed to a second separation system 207, which comprises one or more separation units adapted to separate small catalyst particles from larger catalyst particles. As shown, second separation system 207 selectively separates the first small catalyst stream 205 into a second small catalyst stream 208 and a second large catalyst stream 209. Second small catalyst stream 208 has a median particle diameter less than the median particle diameter of the first small catalyst stream 205, and second large catalyst stream 209 has a median particle diameter greater than the median particle diameter of the first small catalyst stream 205. Ideally, the second large catalyst stream 209 has a desirable median particle diameter, e.g., a heart cut, for converting feedstock 201 to product in reaction system 202. Thus, second large catalyst stream 209 preferably is returned to reaction system 202 to catalyze further conversion of the feedstock 201 to product. First large catalyst stream 206 and/or second small catalyst stream 208 optionally are recycled to a catalyst formulating facility or disposed of.

FIG. 3 illustrates another embodiment of the present invention, wherein small and large catalyst particles are selectively removed from a reaction system to form a population of desirably-sized catalyst particles, which are directed back to the reaction system. Specifically, a feedstock 301, which preferably contains an oxygenate such as methanol or ethanol, is directed to a reaction system 302. In the reaction system 302, a first portion of catalyst particles contacts the feedstock 301 under conditions effective to convert at least a portion of the feedstock 301 to product, which exits the reaction system 302 in a reaction effluent stream, not shown. The reaction system 302 includes a reaction unit and optionally one or more of the following units: a disengaging unit, a catalyst stripper, a catalyst regenerator, a catalyst cooler, and/or conduit lines transferring catalyst particles between these units.

A second portion of catalyst particles 303 (e.g., a portion of the first portion of catalyst particles) is withdrawn from the reaction system 302 and is directed to a first separation system 304. First separation system 304 comprises one or more separation units, which are adapted to separate small catalyst particles from larger catalyst particles. As shown, first separation system 304 selectively separates the second portion of catalyst particles 303 into a first small catalyst stream 305 and a first large catalyst stream 306. First small catalyst stream 305 has a median particle diameter less than the median particle diameter of the second portion of catalyst particles 303, and first large catalyst stream 306 has a median particle diameter greater than the median particle diameter of the second portion of catalyst particles 303.

First large catalyst stream 306 is directed to a second separation system 307, which comprises one or more separation units adapted to separate large catalyst particles from smaller catalyst particles. As shown, second separation system 307 selectively separates the first large catalyst stream 306 into a second small catalyst stream 308 and a second large catalyst stream 309. Second small catalyst stream 308 has a median particle diameter less than the median particle diameter of the first large catalyst stream 306, and second large catalyst stream 309 has a median particle diameter greater than the median particle diameter of the first large catalyst stream 306. Ideally, the second small catalyst stream 308 has a desirable median particle diameter, e.g., a heart cut, for converting feedstock 301 to product in reaction system 302. Thus, second small catalyst stream 308 preferably is returned to reaction system 302 to catalyze further conversion of feedstock 301 to product. First small catalyst stream 305 and/or second large catalyst stream 309 optionally are recycled to a catalyst formulating facility or disposed of.

Figure 5:
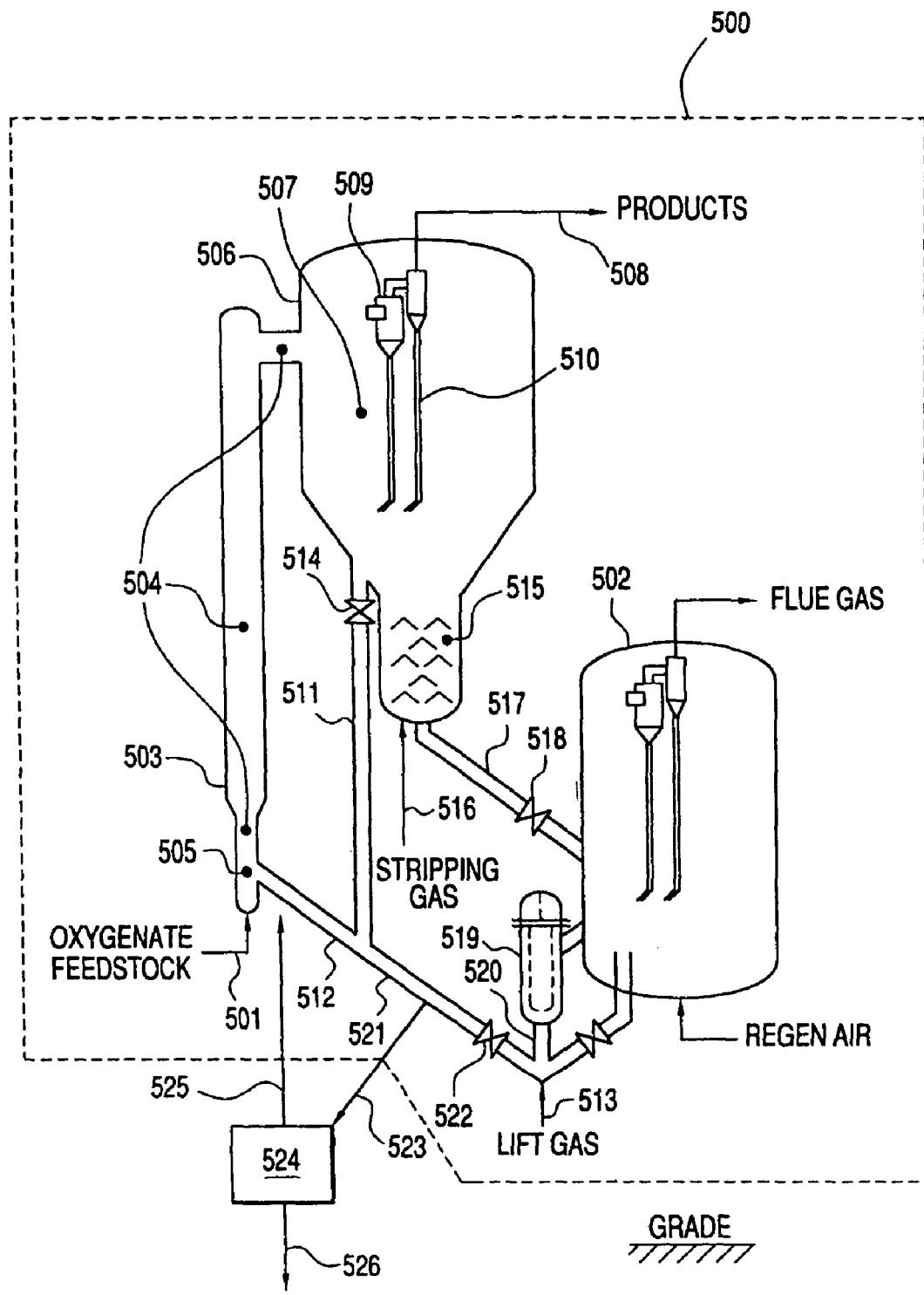
FIG. 5 illustrates an oxygenate to olefin reaction system and a separation system according to one embodiment of the present invention.

FIG. 5 illustrates a detailed schematic diagram of a reaction system 500 in fluid communication with a separation system 524 according to one embodiment of the present invention. As shown, an oxygenate feedstock, comprising at least some oxygenates in a vaporized form, is supplied through line 501 to a reaction unit 503. The reaction unit 503 defines a reaction zone 504 comprising an inlet zone 505, containing fluidizable catalyst particles. An oxygenate conversion reaction takes place in and products including prime olefins are formed in reaction zone 504. At least a portion of the fluidizable catalyst particles are carried from reaction zone 504 to disengaging unit 506, which defines disengaging zone 507. In disengaging zone 507, catalyst particles are separated from the products of the oxygenate conversion reaction, which are yielded from the disengaging zone 507 through line 508. Disengaging zone 507 is of substantially larger cross sectional area than the reaction zone 504, thus significantly slowing the gas superficial velocity in the disengaging zone 507 and allowing a large portion of the catalyst to settle downward with gravity and become largely separated from the oxygenate conversion products and any diluent or unconverted oxygenate conversion feedstock that may be present. A portion of the catalyst particles, which may be entrained with the products of the oxygenate conversion reaction, are carried into a separator device 509, preferably comprising one or more cyclone separators. In the separator device 509, catalyst particles are separated from the oxygenate conversion products, and any diluent or unconverted oxygenate conversion feedstock that may be present. The separated catalyst particles fall into one or more diplegs 510, which direct the separated catalyst particles to disengaging zone 507. A portion of the catalyst from disengaging zone 507 may flow into an optional catalyst recirculation line 511, and subsequently into line 512 where it joins catalyst coming from catalyst regenerator 502. As shown, catalyst in line 521 and line 512 is lifted against gravity with a lift gas, which enters via line 513, and which transports the catalyst to inlet zone 505. Optionally, a control valve 514 may be used on catalyst recirculation line 511.

Another portion of the catalyst from disengaging zone 507 may flow into a catalyst stripper 515, which in this example is also contained within disengaging unit 506. Catalyst stripper 515 optionally contains various elements to enhance stripping action, such as trays, typically shed trays and other elements well known to those skilled in the art. A stripping gas may be introduced via line 516 into the catalyst stripper 515 to enhance removal of interstitial hydrocarbons, entrained oxygenate conversion products and any unconverted oxygenate feedstock from the catalyst prior to sending the catalyst to catalyst regenerator 502, typically by gravity via line 517. Optionally, a control valve 518 may be used in line 517. Gaseous materials may flow up from catalyst stripper 515 into disengaging zone 507. Regenerated catalyst may be returned to inlet zone 505, in this example after having been cooled in catalyst cooler 519, passing through a line 520 in fluid communication with another line 521, and joining with the catalyst being recirculated through the disengaging zone 507 in line 512. Optionally, a control valve 522 may be used in line 521. Oxygenate conversion products from the oxygenate conversion reaction in reaction zone 504 and any unconverted oxygenate feedstock are removed from the reaction system 500 in line 508. Some small measure of such materials may be introduced into the catalyst regenerator 502 due to the imperfect nature of stripping in catalyst stripper 515.

In a preferred embodiment, not shown, the catalyst cooler 519 operates in a closed loop with catalyst regenerator 502. That is, in this embodiment, catalyst cooler 519 receives catalyst from the catalyst regenerator 502 and directs a cooled catalyst back to the catalyst regenerator 502.

According to the present invention, as described above, a portion of the catalyst particles from a reaction system 500 are withdrawn therefrom and directed to a separation system 524, wherein undesirably-sized catalyst particles are removed. As shown in FIG. 5, a portion of catalyst particles are removed from line 521 and directed through line 523 to the separation system 524. The separation system 524 may be formed of one or more size-selective separation units, the arrangement of which is described in detail above with reference to FIGS. 1–3. Moreover, separation system 524 optionally operates to selectively remove large particles, small particles, or both, from the reaction system 500. Selectively separated catalyst particles that have an undesirable size (e.g., an undesirable median particle diameter) are removed from the separation system 524 through line 526, while particles having a desirable size or median particle diameter are returned to the reaction system 500 via line 525.

Although the separation system 524 illustrated in FIG. 5 receives catalyst particles from line 521, which returns catalyst particles to the reaction unit 503, the portion of catalyst particles that are to be separated in the separation system 524 may be withdrawn from a variety of regions of the reaction system 500 without deviating in scope from the present invention. For example, the separation system 524 optionally receives catalyst particles from one more of the following portions of the reaction system: reaction unit 503 (e.g., from inlet zone 505 and/or from reaction zone 504), disengaging unit 506 (e.g., from disengaging zone 507), separation device 509 (e.g., from dipleg 510), catalyst stripper 515, catalyst regenerator 502, catalyst cooler 519, and/or from one or more of lines 511, 517, 521 and/or 512.

Similarly, desirable-sized catalyst particles may be directed from separation system 524 to one or more of the following regions of the reaction system 500 via line 525: reaction unit 503 (e.g., to inlet zone 505 and/or to reaction zone 504), disengaging unit 506 (e.g., to disengaging zone 507), separation device 509, catalyst stripper 515, catalyst regenerator 502, catalyst cooler 519, and/or from one or more of lines 511, 517, 521 and/or 512.

Exemplary Separation Devices

Any of a number of separation units may be implemented according to the present invention to separate a plurality of catalyst particles into a small catalyst stream and a large catalyst stream. A non-limiting exemplary list of separation units that may be used according to the present invention include: cyclone separators, settling vessels, screens, and air classifiers.

The design and operation of cyclone separators are known to those skilled in the art. See, for example, U.S. Pat. Nos. 5,518,695; 5,290,431; 4,904,281; 4,670,410; 2,934,494 and 2,535,140, the entireties of which are all incorporated herein by reference. In the operation of a cyclone separator, vapor components and optionally a minor amount of entrained particulates are urged by pneumatic pressure up the cyclone separator and through a top outlet, while heavier particles, by virtue of their inertia and centrifugal force, tend to move toward the outside separator wall, from which they are urged by gravity in a downward direction into a receiver and ultimately through a large particle stream outlet. The centrifugal separating force for acceleration may range from 5 times gravity in very large diameter, low resistance cyclones, to 2500 times gravity in very small high resistance units.

Specifically, gaseous material and a collection of particulate material enter the cyclone separator through a tangentially oriented inlet. The collection of particulate material preferably comprises catalyst particles of varying sizes; some particles being larger and/or smaller than others. Tangential entry of the gaseous and particulate material creates a swirling action of the gaseous and particulate material inside the cyclone separator and establishes an inner vortex pattern and an outer vortex pattern.

Centrifugal acceleration of the particulate material in the cyclone separator tends to urge larger particulate material outwardly to the wall of the of the cyclone separator. As a result, the outer vortex pattern tends to comprise a greater amount of the larger particulate material than the inner vortex, which comprises gaseous components and smaller particulate material, e.g., catalyst fines. In addition to centrifugal forces, gravity tends to urge the larger particulate material in the outer vortex downward. In one embodiment, the larger particulate material falls along the wall of the cyclone separator and collects in a hopper of the cyclone separator. The collected particulate material optionally is then directed to a recycling facility, wherein the collected particulate material is formulated into a catalyst composition having desirable particle size characteristics. Optionally, all or a portion of the larger catalyst particles are directed back to the reaction unit.

At some point within the cyclone separator, the outer vortex terminates and the inner vortex is formed, which comprises gaseous components and smaller particulate material. The inner vortex progresses upwardly through the cyclone separator under pneumatic pressure and enters an outlet tube, also referred to herein as an inner hollow cylindrical member, which preferably is attached to a laterally extending top surface, which defines the top of the cyclone separator. The outlet tube optionally has a diameter that approximates the outer periphery of the inner cyclone vortex. Optionally, the outlet tube traverses the laterally-extending top surface of the cyclone separator and extends downwardly into the inner volume of the cyclone separator in order to facilitate size-selective separation. Optionally, all or a portion of the smaller catalyst particles are directed back to the reaction unit.

Structurally, the cyclone separator preferably includes an outer hollow cylindrical member having a laterally extending top surface at its distal end and an open end at its proximal end. As used herein, a proximal end of a specified component is that end of the component that is nearest to grade. Conversely, the distal end of a specified component is that end of the component that is furthest removed from grade. The open end of the outer hollow cylindrical member preferably is in open communication with a hollow conical member having a broad distal end that narrows into a narrow proximal end. The narrow proximal end of the hollow conical member preferably forms an opening at its apex. The apex opening optionally is in open communication with a standpipe which is adapted to transport large particulate material.

The outlet tube preferably traverses the laterally extending top surface of the cyclone separator and extends into the inner volume formed by the outer hollow cylindrical member. At its proximal end, the inner hollow cylindrical member includes a small stream outlet, which preferably is adapted to receive small components from the inner vortex created within the cyclone separator. The outer hollow cylindrical member also includes an inlet, which is adapted to receive a particulate laden stream from the reaction system. Ideally, the inlet to the outer hollow cylindrical member introduces the particle laden stream in a tangential manner with respect to the outer hollow cylindrical member such that as the particulate laden stream is introduced into the outer hollow cylindrical member it forms an outer vortex within the outer hollow cylindrical member.

In operation, as catalyst particles are introduced into the cyclone separator, the larger catalyst particles are urged along the inner surface of the outer hollow cylindrical member, while the smaller catalyst particles, due to their lower mass, tend to become entrained with the gaseous components and form the inner vortex within the cyclone separator. Gravity and centrifugal forces tend to direct the larger and heavier catalyst particles from the outer hollow cylindrical member through its open end and into the hollow conical member. The hollow conical member tends to direct the larger catalyst particles from the outer hollow cylindrical member to the apex opening and optionally to a standpipe. Smaller components that were introduced into the separator inlet tend to be forced into small stream outlet and into the inner hollow cylindrical member by pneumatic forces. In this manner, smaller particles and gaseous components that enter the cyclone separator tend to separated from heavier particulate materials.

In a particularly preferred embodiment of the present invention, the separation unit comprises a counter flow cyclone separator. A counter flow cyclone separator operates in a manner similar to a normal cyclone separator. However, in a counter flow cyclone separator, the heavier catalyst particles that flow along the outer wall of the cyclone separator, e.g., the outer vortex, contact a turbulizing stream, which creates a turbulent environment within the counter flow cyclone separator. The formation of a turbulent environment within the counter flow cyclone separator tends to urge smaller particulate materials, that may have become entrained with the larger catalyst particles in the outer vortex, into the inner vortex and ultimately out of the counter flow cyclone separator with the gaseous and smaller particulate components present in the inner vortex. That is, the turbulizing stream causes a portion of the particles in the outer vortex (typically, smaller particles) to be transferred to the inner vortex.

Specifically, in the counter flow cyclone separator, a particulate laden stream enters an outer hollow cylindrical member or hollow conical member tangentially at one or more separator inlets. As with conventional cyclones, tangential entry of the gaseous and particulate material creates a swirling action of the gaseous and particulate material inside the counter flow cyclone separator and establishes an inner vortex pattern and an outer vortex pattern. Centrifugal acceleration of the particulate material in the cyclone separator tends to urge larger particulate material outwardly to the wall of the of the cyclone separator. As a result, the outer vortex pattern tends to comprise a greater amount of the larger particulate material than the inner vortex, which comprises gaseous components and smaller particulate material, e.g., catalyst fines. In addition to centrifugal forces, gravity tends to urge the larger particulate materials in the outer vortex downward. The outer vortex, however, may contain a minor amount of entrained smaller or medium sized particles, a portion of which optionally are transferred to the inner vortex, described below, by the turbulizing stream.

At some point within the counter flow cyclone separator, the outer vortex terminates and an inner vortex is formed, which comprises gaseous components and smaller particulate material. The inner vortex progresses upwardly through the cyclone separator under pneumatic pressure and enters an inner hollow cylindrical tube, also referred to herein as an "outlet tube", which preferably is attached to a laterally extending top surface that defines the top of the cyclone separator. The outlet tube optionally has a diameter that approximates the outer periphery of the inner cyclone vortex. Optionally, the outlet tube traverses the laterally-extending top surface of the counter flow cyclone separator and extends downwardly into the inner volume of the cyclone separator in order to facilitate size-selective separation. Optionally, all or a portion of the smaller catalyst particles are directed back to the reaction unit.

Structurally, the counter flow cyclone separator preferably includes an outer hollow cylindrical member having a laterally extending top surface at its distal end and an open end at its proximal end. The open end of the outer hollow cylindrical member preferably is in open communication with a hollow conical member having a broad distal end that narrows into a narrow proximal end. The narrow proximal end of the hollow conical member preferably forms an opening at its apex. The apex opening optionally is in open communication with a standpipe which is adapted to transport large particulate material away from the counter flow cyclone separator.

Additionally, the counter flow cyclone separator comprises a second inlet for receiving a turbulizing stream. The second inlet optionally is situated on the outer hollow cylindrical member or the hollow conical member. The second inlet optionally introduces the turbulizing stream into one or more of the outer hollow cylindrical member or the hollow conical member. Inside the counter flow cyclone separator, at least a portion of the plurality of catalysts particles in the outer vortex contacts the turbulizing stream under conditions effective to the separate some smaller catalyst particles from the outer vortex. At least a portion of these separated smaller catalyst particles become entrained with the inner vortex and exit the cyclone separator through the outlet tube with the gaseous and smaller catalyst particles.

The second inlet preferably receives the turbulizing stream from a turbulizing stream storage unit, e.g., a pressurized tank or other storage vessel, or from a conduit in fluid communication with a plant utility line, such as an air or nitrogen-containing stream. A turbulizing stream conduit line transports the turbulizing stream from the storage tank or plant utility line to the second inlet. Preferably the turbulizing stream conduit includes one or more flow control valves adapted to adjustably control the flow of turbulizing stream that is introduced into the counter flow cyclone separator, depending upon the desired separation characteristics.

In operation, as the turbulizing stream is introduced via the second inlet into the counter flow cyclone separator, the turbulizing stream tends to disturb the cyclone formed by the catalyst particles in the counter flow cyclone separator in a turbulent manner. By disturbing the flow of catalyst particles in the counter flow cyclone separator, smaller catalyst particles tend to be transferred from the outer vortex to the inner vortex and ultimately enter the small stream outlet defined by the inner hollow cylindrical member. Notwithstanding the introduction of the turbulizing stream into the counter flow cyclone separator, larger catalyst particles will tend to continue to be transported through the standpipe and ultimately out of the large stream outlet. Optionally, all or a portion of these larger catalyst particles are directed back to the reaction unit.

Thus, unlike conventional cyclone separators, a counter flow cyclone separator tends to facilitate the removal of smaller catalyst particles that have become entrained with the larger catalyst particles in the outer vortex. Advantageously, if the counter flow cyclone separator includes one or more flow control valves about the turbulizing stream conduit line, then the particle size distribution of the small catalyst stream, which exits the counter flow cyclone separator via the small stream outlet, is fully controllable by the actuation of the one or more flow control valves. In another preferred embodiment, the counter flow cyclone separator includes a plurality of hollow conical members and a plurality of cylindrical members, preferably arranged in an alternating manner. Optionally, a plurality of counter flow cyclone separators may be in open communication with one another to facilitate the separation of undesirably-sized catalyst particles from desirably-sized catalyst particles.

The turbulizing stream that is implemented according to the present invention may vary widely. An exemplary non-limiting list of turbulizing streams includes: air, nitrogen, steam, flue gas and mixtures thereof. Optionally, the inner hollow cylindrical member is in open communication with a scroll outlet which deviates the flow of the small catalyst stream by about 90°.

Figure 4:
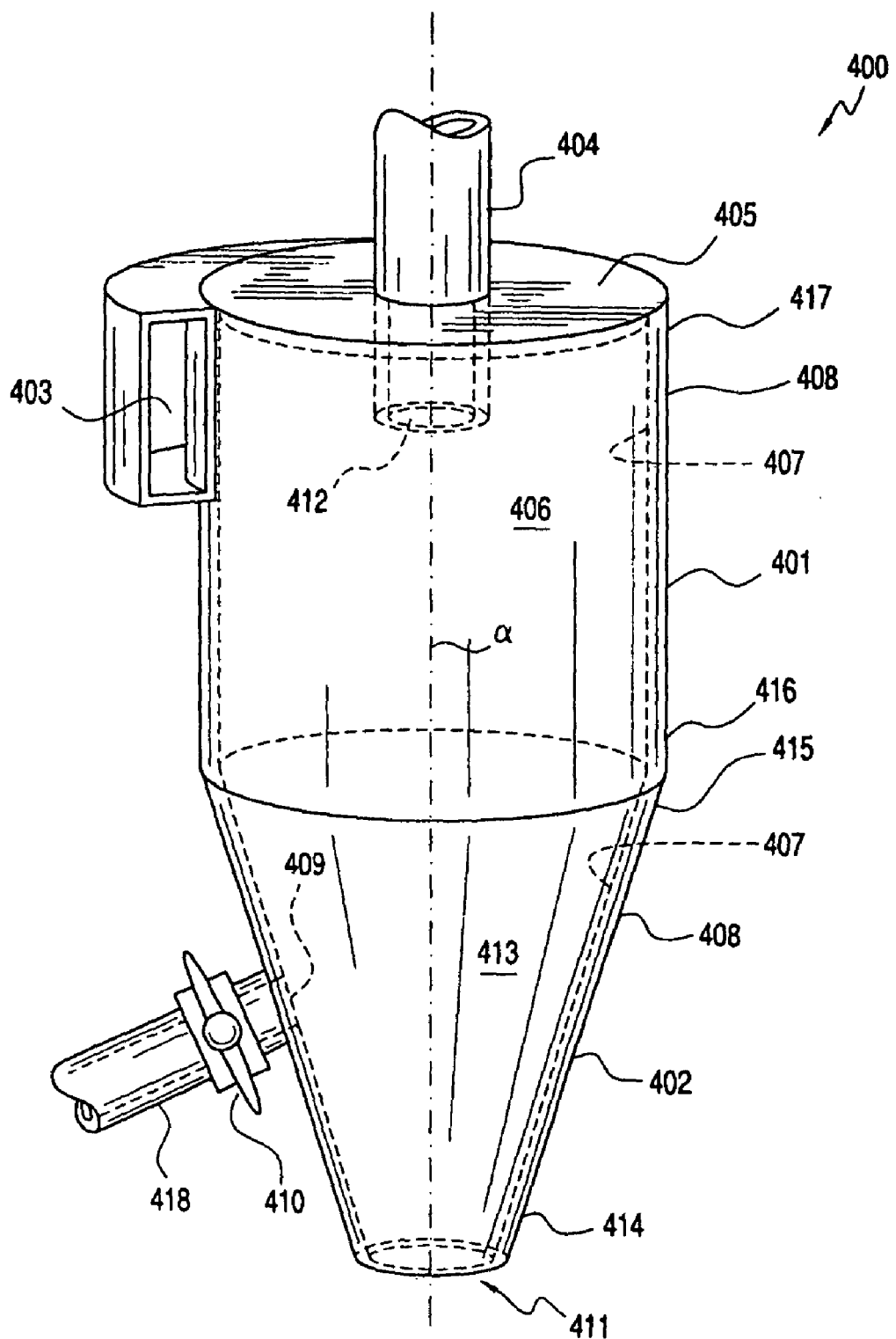
FIG. 4 illustrates a size selective separation device that optionally is implemented according to the present invention.

FIG. 4 illustrates a counter flow cyclone separator, generally designated 400. As shown, the counter flow cyclone separator 400 comprises an outer hollow cylindrical member 401, a hollow conical member 402, an inlet 403, and an inner hollow cylindrical member 404, e.g., an outlet tube. Outer hollow cylindrical member 401 includes a proximal end 416 and a distal end 417, and forms a wall defining an inner volume 406. The wall formed by the outer hollow cylindrical member 401 has an inner surface 407 and an outer surface 408. The proximal end 416 of outer hollow cylindrical member 401 is in open communication with hollow conical member 402, which also has an inner surface 407 and an outer surface 408. The distal end 417 of outer hollow tubular member 401 is limited, in part, by a laterally-extending top surface 405, also having an inner surface and an outer surface.

Outer hollow cylindrical member 401 is also in open communication with an inlet 403, which preferably is situated in a tangential manner with respect to the outer surface 408 of the outer hollow tubular member 401. In operation, the inlet 403 receives a catalyst-containing stream from a reaction system in a tangential manner and forms an inner vortex, containing smaller components, formed about the longitudinally extending center axis a in inner volumes 406 and 413. The inlet also creates an outer vortex in inner volumes 406 and 413, containing larger catalyst particles. The outer vortex is coaxial with and surrounds the inner vortex and is coaxial with center axis a. The outer limits of the outer vortex are limited by the inner surface 407 of the outer hollow cylindrical member 401 and by the inner surface 407 of the hollow conical member 402.

As shown, the inner hollow tubular member 404 traverses the top surface 405 and extends into inner volume 406. The proximal end of the inner hollow tubular member 404 forms an opening 412 (e.g., the small stream outlet) adapted to receive an inner vortex formed in the counter flow cyclone separator 400, which inner vortex comprises lighter components received in the counter flow cyclone separator 400.

Hollow conical member 402 includes a broad distal end 415 and a narrow proximal end 414, and forms a wall defining inner volume 413. The wall formed by the conical member 402, which is continuous with the wall defined by the outer hollow cylindrical member 401, also has an inner surface 407 and an outer surface 408. Narrow proximal end 414 forms apex opening 411, through which the larger particulate materials, contained in the outer vortex, are yielded from the counter flow cyclone separator 400.

Hollow conical member 402 preferably defines a second inlet 409, which is in open communication with a turbulizing stream conduit 418. Turbulizing stream conduit 418 receives a turbulizing stream from a turbulizing stream source, not shown, and directs the turbulizing stream to second inlet 409. In operation, the turbulizing stream flows through the hollow conical member 402 and enters inner volume 413, thereby at least partially disrupting the downward flow of the outer vortex. In this manner, a portion of the lighter particulate components entrained in the outer vortex are removed therefrom and are transferred to the inner vortex for removal from the counter flow cyclone separator 400 via opening 412 and inner hollow cylindrical member 404. Turbulizing stream conduit 418 optionally includes a control valve 410 to control the flow rate of the turbulizing stream into the counter flow cyclone separator 400. Control of the particle size "cut" can be desirably achieved by modulation of the turbulizing stream flow rate into counter flow cyclone separator 400.

Oxygenate to Olefin Reaction Systems

As indicated above, the present invention is particularly well-suited for implementation into an oxygenate to olefin (OTO) reaction system, which will now be described in greater detail. In the OTO reaction process, an oxygenate, e.g., methanol, contacts a molecular sieve catalyst composition in a reaction unit, under conditions effective to convert at least a portion of the oxygenate to light olefins.

The catalyst compositions to be separated according to the present invention are useful in a variety of processes including: cracking, of for example a naphtha feed to light olefin(s) (U.S. Pat. No. 6,300,537) or higher molecular weight (MW) hydrocarbons to lower MW hydrocarbons; hydrocracking, of for example heavy petroleum and/or cyclic feedstock; isomerization, of for example aromatics such as xylene, polymerization, of for example one or more olefin(s) to produce a polymer product; reforming; hydrogenation; dehydrogenation; dewaxing, of for example hydrocarbons to remove straight chain paraffins; absorption, of for example alkyl aromatic compounds for separating out isomers thereof; alkylation, of for example aromatic hydrocarbons such as benzene and alkyl benzene, optionally with propylene to produce cumeme or with long chain olefins; transalkylation, of for example a combination of aromatic and polyalkylaromatic hydrocarbons; dealkylation; hydrodecylization; disproportionation, of for example toluene to make benzene and paraxylene; oligomerization, of for example straight and branched chain olefin(s); and dehydrocyclization.

Preferred processes are conversion processes including: naphtha to highly aromatic mixtures; light olefin(s) to gasoline, distillates and lubricants; oxygenates to olefin(s); light paraffins to olefins and/or aromatics; and unsaturated hydrocarbons (ethylene and/or acetylene) to aldehydes for conversion into alcohols, acids and esters. The most preferred process of the invention is a process directed to the conversion of a feedstock comprising one or more oxygenates to one or more olefin(s).

Molecular sieve catalyst compositions are particularly useful in conversion processes of different feedstock. Typically, the feedstock contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as dimethyl ether, diethyl ether and methylethyl ether, alkyl-halides such as methyl chloride and ethyl chloride, alkyl ketones such as dimethyl ketone, formaldehydes, and various acids such as acetic acid.

In a preferred embodiment of the process of the invention, the feedstock comprises one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene. Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition of the invention into olefin(s) having 2 to 6 carbons atoms, preferably 2 to 4 carbon atoms. Most preferably, the olefin(s), alone or in combination, are converted from a feedstock containing an oxygenate, preferably an alcohol, most preferably methanol, to the preferred olefin(s) ethylene and/or propylene.

There are many processes used to convert feedstock into olefin(s) including various cracking processes such as steam cracking, thermal regenerative cracking, fluidized bed cracking, fluid catalytic cracking, deep catalytic cracking, and visbreaking. The most preferred process is generally referred to as gas-to-olefins (GTO) or alternatively, methanol-to-olefins (MTO). In a GTO process, typically natural gas is converted into a synthesis gas that is converted into an oxygenated feedstock, preferably containing methanol, where the oxygenated feedstock is converted in the presence of a molecular sieve catalyst composition into one or more olefin(s), preferably ethylene and/or propylene. In an OTO reaction process, typically an oxygenated feedstock, most preferably a methanol-containing feedstock, is converted in the presence of a molecular sieve catalyst composition thereof into one or more olefin(s), preferably and predominantly, ethylene and/or propylene, often referred to as light olefin(s).

In one embodiment of the process for conversion of a feedstock, preferably a feedstock containing one or more oxygenates, the amount of olefin(s) produced based on the total weight of hydrocarbon produced is greater than 50 weight percent, preferably greater than 60 weight percent, more preferably greater than 70 weight percent, and most preferably greater than 75 weight percent. In another embodiment of the process for conversion of one or more oxygenates to one or more olefin(s), the amount of ethylene and/or propylene produced based on the total weight of hydrocarbon product produced is greater than 65 weight percent, preferably greater than 70 weight percent, more preferably greater than 75 weight percent, and most preferably greater than 78 weight percent.

In another embodiment of the process for conversion of one or more oxygenates to one or more olefin(s), the amount ethylene produced in weight percent based on the total weight of hydrocarbon product produced, is greater than 30 weight percent, more preferably greater than 35 weight percent, and most preferably greater than 40 weight percent. In yet another embodiment of the process for conversion of one or more oxygenates to one or more olefin(s), the amount of propylene produced in weight percent based on the total weight of hydrocarbon product produced is greater than 20 weight percent, preferably greater than 25 weight percent, more preferably greater than 30 weight percent, and most preferably greater than 35 weight percent.

The feedstock, in one embodiment, contains one or more diluent(s), typically used to reduce the concentration of the feedstock, and are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

The diluent optionally is used either in a liquid or a vapor form, or a combination thereof. The diluent is either added directly to a feedstock entering into a reaction unit or added directly into a reaction unit, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, and most preferably from about 5 to about 25.

In one embodiment, other hydrocarbons are added to a feedstock either directly or indirectly, and include olefin(s), paraffin(s), aromatic(s) (see for example U.S. Pat. No. 4,677,242) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reaction unit, where the process is a fixed bed process, a fluidized bed process (includes a turbulent bed process), preferably a continuous fluidized bed process, and most preferably a continuous high velocity fluidized bed process.

The reaction processes can take place in a variety of catalytic reaction units such as hybrid reaction units that have a dense bed or fixed bed reaction zones and/or fast fluidized bed reaction zones coupled together, circulating fluidized bed reaction units, riser reactors, and the like. Suitable conventional reaction units are described in for example U.S. Pat. No. 4,076,796, U.S. Pat. No. 6,287,522, and Fluidization Engineering, D. Kunii and O. Levenspiel, Robert E. Krieger Publishing Company, New York, N.Y. 1977, which are all herein fully incorporated by reference. The preferred reaction unit includes riser reactors generally described in Riser Reactor, Fluidization and Fluid-Particle Systems, pages 48 to 59, F. A. Zenz and D. F. Othmo, Reinhold Publishing Corporation, New York, 1960, and U.S. Pat. No. 6,166,282, and U.S. patent application Ser. No. 09/564,613 filed May 4, 2000, which are all herein fully incorporated by reference.

The reaction system preferably comprises a fluid bed reaction system having a first reaction zone within one or more riser reactor(s) and a second reaction zone within at least one disengaging unit, preferably comprising one or more cyclones. In one embodiment, the one or more riser reactor(s) and disengaging unit are contained within a single vessel. Fresh feedstock, preferably containing one or more oxygenates, optionally with one or more diluent(s), is fed to the one or more reaction units (preferably riser reactor(s)) in which a molecular sieve catalyst composition or coked version thereof is introduced. In one embodiment, the molecular sieve catalyst composition or coked version thereof is contacted with a liquid or gas, or combination thereof, prior to being introduced to the reaction unit(s). Preferably the liquid is water or methanol, and the gas is an inert gas such as nitrogen.

In an embodiment, the amount of liquid feedstock fed separately or jointly with a vapor feedstock to a reaction system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably of similar or the same composition, or contain varying proportions of the same or different feedstock with the same or different diluent.

The feedstock entering the reaction unit is preferably converted, partially or fully, in the first reaction zone into a gaseous effluent that enters the disengaging unit along with a coked molecular sieve catalyst composition. In the preferred embodiment, cyclone(s) within the disengaging unit are designed to separate the molecular sieve catalyst composition, preferably a coked molecular sieve catalyst composition, from the gaseous effluent containing one or more olefins within the disengaging zone. Cyclones are preferred, however, gravity effects within the disengaging unit will also separate the catalyst compositions from the gaseous effluent. Other methods for separating the catalyst compositions from the gaseous effluent include the use of plates, caps, elbows, and the like.

In one embodiment, the disengaging unit includes a catalyst stripper at its lower portion. In the catalyst stripper, the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then optionally introduced to a catalyst regenerator. In another embodiment, the catalyst stripper is in a separate vessel from the disengaging unit and the gas is passed at a gas hourly superficial velocity (GHSV) of from 1 hr-1 to about 20,000 hr-1 based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reaction system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C. most preferably from about 350° C. to about 550° C.

The conversion pressure employed in the conversion process, specifically within the reaction system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reaction unit.

Typically, the WHSV ranges from about 1 hr-1 to about 5000 hr-1, preferably from about 2 hr-1 to about 3000 hr-1, more preferably from about 5 hr-1 to about 1500 hr-1, and most preferably from about 10 hr-1 to about 1000 hr-1. In one preferred embodiment, the WHSV is greater than 20 hr-1, preferably the WHSV for conversion of a feedstock containing methanol and dimethyl ether is in the range of from about 20 hr-1 to about 300 hr-1.

The superficial gas velocity (SGV) of the feedstock including diluent and reaction products within the reaction system is preferably sufficient to fluidize the molecular sieve catalyst composition within a reaction zone in the reaction unit. The SGV in the process, particularly within the reaction system, more particularly within the one or more reaction units, is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec.

In one preferred embodiment of the process for converting an oxygenate to olefin(s) using a silicoaluminophosphate molecular sieve catalyst composition, the process is operated at a WHSV of at least 20 hr-1 and a Temperature Corrected Normalized Methane Selectivity (TCNMS) of less than 0.016, preferably less than or equal to 0.01. See for example U.S. Pat. No. 5,952,538, which is herein fully incorporated by reference. In another embodiment of the processes for converting an oxygenate such as methanol to one or more olefin(s) using a molecular sieve catalyst composition, the WHSV is from 0.01 hr-1 to about 100 hr-1, at a temperature of from about 350° C. to 550° C., and silica to Me2O3 (Me is a Group IIIA or VIII element from the Periodic Table of Elements) molar ratio of from 300 to 2500. See for example EP-0 642 485 B1, which is herein fully incorporated by reference. Other processes for converting an oxygenate such as methanol to one or more olefin(s) using a molecular sieve catalyst composition are described in PCT WO 01/23500 published Apr. 5, 2001 (propane reduction at an average catalyst feedstock exposure of at least 1.0), which is herein incorporated by reference.

The coked molecular sieve catalyst composition is withdrawn from the disengaging unit, preferably by one or more cyclones(s), and introduced to a regeneration system. The regeneration system comprises a catalyst regenerator where the coked catalyst composition is contacted with a regeneration medium, preferably a gas containing oxygen, under general regeneration conditions of temperature, pressure and residence time. Non-limiting examples of the regeneration medium include one or more of oxygen, O3, SO3, N2O, NO, NO2, N2O5, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the catalyst regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa). The preferred residence time of the molecular sieve catalyst composition in the regenerator is in the range of from about one minute to several hours, most preferably about one minute to 100 minutes, and the preferred volume of oxygen in the gas is in the range of from about 0.01 mole percent to about 5 mole percent based on the total volume of the gas.

In one embodiment, regeneration promoters, typically metal containing compounds such as platinum, palladium and the like, are added to the catalyst regenerator directly, or indirectly, for example with the coked catalyst composition. Also, in another embodiment, a fresh molecular sieve catalyst composition is added to the catalyst regenerator containing a regeneration medium of oxygen and water as described in U.S. Pat. No. 6,245,703, which is herein fully incorporated by reference. In yet another embodiment, a portion of the coked molecular sieve catalyst composition from the catalyst regenerator is returned directly to the one or more reaction units, or indirectly, by pre-contacting with the feedstock, or contacting with fresh molecular sieve catalyst composition, or contacting with a regenerated molecular sieve catalyst composition or a cooled regenerated molecular sieve catalyst composition described below.

The burning of coke is an exothermic reaction, and in an embodiment, the temperature within the regeneration system is controlled by various techniques in the art including feeding a cooled gas to the catalyst regenerator, operated either in a batch, continuous, or semi-continuous mode, or a combination thereof. A preferred technique involves withdrawing the regenerated molecular sieve catalyst composition from the catalyst regeneration and passing the regenerated molecular sieve catalyst composition through a catalyst cooler that forms a cooled regenerated molecular sieve catalyst composition. The catalyst cooler, in an embodiment, is a heat exchanger that is located either internal or external to the catalyst regenerator. In one embodiment, the cooled regenerated molecular sieve catalyst composition is returned to the catalyst regenerator in a continuous cycle. Alternatively, (see U.S. patent application Ser. No. 09/587,766 filed Jun. 6, 2000) a portion of the cooled regenerated molecular sieve catalyst composition is returned to the catalyst regenerator in a continuous cycle, and another portion of the cooled molecular sieve regenerated molecular sieve catalyst composition is returned to the reaction unit(s), directly or indirectly, or a portion of the regenerated molecular sieve catalyst composition or cooled regenerated molecular sieve catalyst composition is contacted with by-products within the gaseous effluent (PCT WO 00/49106 published Aug. 24, 2000). In another embodiment, a regenerated molecular sieve catalyst composition contacts an alcohol, preferably ethanol, 1-propnaol, 1-butanol or mixture thereof, and is introduced to the reaction system, as described in U.S. patent application Ser. No. 09/785,122 filed Feb. 16, 2001, which is herein fully incorporated by reference. Other methods for operating a regeneration system are disclosed in U.S. Pat. No. 6,290,916, which is herein fully incorporated by reference.

The regenerated molecular sieve catalyst composition withdrawn from the catalyst regenerator, preferably from the catalyst cooler, is combined with a fresh molecular sieve catalyst composition and/or re-circulated molecular sieve catalyst composition and/or feedstock and/or fresh gas or liquids, and returned to the reaction unit(s). In another embodiment, the regenerated molecular sieve catalyst composition withdrawn from the regeneration system is returned to the reaction units(s) directly, optionally after passing through a catalyst cooler. In one embodiment, a carrier, such as an inert gas, feedstock vapor, steam or the like, semi-continuously or continuously, facilitates the introduction of the regenerated molecular sieve catalyst composition to the reaction unit, preferably to one or more riser reactors.

In one embodiment, by controlling the flow of the regenerated molecular sieve catalyst composition or cooled regenerated molecular sieve catalyst composition from the catalyst regenerator to the reaction unit, the optimum level of coke on the molecular sieve catalyst composition in the reaction zone is maintained. There are many techniques for controlling the flow of a molecular sieve catalyst composition described in Michael Louge, Experimental Techniques, Circulating Fluidized Beds, Grace, Avidan and Knowlton, eds., Blackie, 1997 (336–337), which is herein incorporated by reference. In another embodiment, the optimum level of coke on the molecular sieve catalyst composition in the reaction zone is maintained by controlling the flow rate of oxygen containing gas flowing to the catalyst regenerator, a partial regeneration. Coke levels on the molecular sieve catalyst composition are measured by withdrawing the molecular sieve catalyst composition from the conversion process at a point in the process and determining its carbon content. Typical levels of coke on the molecular sieve catalyst composition, after regeneration is in the range of from 0.01 weight percent to about 15 weight percent, preferably from about 0.1 weight percent to about 10 weight percent, more preferably from about 0.2 weight percent to about 5 weight percent, and most preferably from about 0.3 weight percent to about 2 weight percent based on the total weight of the molecular sieve and not the total weight of the molecular sieve catalyst composition.

In one preferred embodiment, the mixture of fresh molecular sieve catalyst composition and/or regenerated molecular sieve catalyst composition and/or cooled regenerated molecular sieve catalyst composition in the reaction zone contains in the range of from about 1 to 50 weight percent, preferably from about 2 to 30 weight percent, more preferably from about 2 to about 20 weight percent, and most preferably from about 2 to about 10 coke or carbonaceous deposit based on the total weight of the mixture of molecular sieve catalyst compositions. See for example U.S. Pat. No. 6,023,005, which is herein fully incorporated by reference. It is recognized that the molecular sieve catalyst composition in the reaction zone is made up of a mixture of regenerated and fresh molecular sieve catalyst composition that have varying levels of carbon and carbon-like deposits, e.g., coke. The measured level of these deposits, specifically coke, represents an average of the levels on individual molecular sieve catalyst composition particles.

The gaseous effluent is withdrawn from the disengaging unit and is passed through a recovery system. There are many well known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like. Non-limiting examples of these towers, columns, splitters or trains used alone or in combination include one or more of a demethanizer, preferably a high temperature demethanizer, a dethanizer, a depropanizer, preferably a wet depropanizer, a wash tower often referred to as a caustic wash tower and/or quench tower, absorbers, adsorbers, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643, U.S. Pat. Nos. 5,019,143, 5,452,581 and 5,082,481, U.S. Pat. No. 5,672,197, U.S. Pat. No. 6,069,288, U.S. Pat. No. 5,904,880, U.S. Pat. No. 5,927,063, and U.S. Pat. No. 6,121,504, U.S. Pat. No. 6,121,503, and U.S. Pat. No. 6,293,998, which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in a MTO process are passed through a purification system that removes low levels of by-products or contaminants. Non-limiting examples of contaminants and by-products include generally polar compounds such as water, alcohols, carboxylic acids, ethers, carbon oxides, sulfur compounds such as hydrogen sulfide, carbonyl sulfides and mercaptans, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example for the purification of olefin(s), are described in Kirk-Othmer Encyclopedia of Chemical Technology, 4th Edition, Volume 9, John Wiley & Sons, 1996, pages 249–271 and 894–899, which is herein incorporated by reference. Purification systems are also described in for example, U.S. Pat. No. 6,271,428, U.S. Pat. No. 6,293,999, and U.S. patent application Ser. No. 09/689,363 filed Oct. 20, 2000, which are herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent gas withdrawn from the reaction unit or converting those products produced as a result of the recovery system utilized.

In one embodiment, the effluent gas withdrawn from the reaction unit is passed through a recovery system producing one or more hydrocarbon containing stream(s), in particular, a three or more carbon atom (C3+) hydrocarbon containing stream. In this embodiment, the C3+ hydrocarbon containing stream is passed through a first fractionation zone producing a crude C3 hydrocarbon and a C4+ hydrocarbon containing stream, the C4+ hydrocarbon containing stream is passed through a second fractionation zone producing a crude C4 hydrocarbon and a C5+ hydrocarbon containing stream. The four or more carbon hydrocarbons include butenes such as butene-1 and butene-2, butadienes, saturated butanes, and isobutanes.

The effluent gas removed from a conversion process, particularly a MTO process, typically has a minor amount of hydrocarbons having 4 or more carbon atoms. The amount of hydrocarbons having 4 or more carbon atoms is typically in an amount less than 20 weight percent, preferably less than 10 weight percent, more preferably less than 5 weight percent, and most preferably less than 2 weight percent, based on the total weight of the effluent gas withdrawn from a MTO process, excluding water. In particular with a conversion process of oxygenates into olefin(s) utilizing a molecular sieve catalyst composition the resulting effluent gas typically comprises a majority of ethylene and/or propylene and a minor amount of four carbon and higher carbon number products and other by-products, excluding water.

Suitable well known reaction systems as part of the recovery system primarily take lower value products and convert them to higher value products. For example, the C4 hydrocarbons, butene-1 and butene-2 are used to make alcohols having 8 to 13 carbon atoms, and other specialty chemicals. For example, isobutylene is used to make a gasoline additive, methyl-t-butylether, butadiene in a selective hydrogenation unit is converted into butene-1 and butene-2, and butane is useful as a fuel. Non-limiting examples of reaction systems include U.S. Pat. No. 5,955,640, U.S. Pat. No. 4,774,375, U.S. Pat. No. 6,049,017, U.S. Pat. Nos. 4,287,369 and 5,763,678, U.S. Pat. No. 4,542,252, U.S. Pat. No. 5,634,354, and Cosyns, J. et al., Process for Upgrading C3, C4 and C5 Olefinic Streams, Pet. & Coal, Vol. 37, No. 4 (1995), which are all herein fully incorporated by reference.

The preferred light olefin(s) produced by any one of the processes described above, preferably conversion processes, are high purity prime olefin(s) products that contains a single carbon number olefin in an amount greater than 80 percent, preferably greater than 90 weight percent, more preferably greater than 95 weight percent, and most preferably no less than about 99 weight percent, based on the total weight of the olefin. In one embodiment, high purity prime olefin(s) are produced in the process of the invention at rate of greater than 5 kg per day, preferably greater than 10 kg per day, more preferably greater than 20 kg per day, and most preferably greater than 50 kg per day. In another embodiment, high purity ethylene and/or high purity propylene is produced by the process of the invention at a rate greater than 4,500 kg per day, preferably greater than 100,000 kg per day, more preferably greater than 500,000 kg per day, even more preferably greater than 1,000,000 kg per day, yet even more preferably greater than 1,500,000 kg per day, still even more preferably greater than 2,000,000 kg per day, and most preferably greater than 2,500,000 kg per day.

Other conversion processes, in particular, a conversion process of an oxygenate to one or more olefin(s) in the presence of a molecular sieve catalyst composition, especially where the molecular sieve is synthesized from a silicon-, phosphorous-, and alumina-source, include those described in for example: U.S. Pat. No. 6,121,503, U.S. Pat. No. 6,187,983, PCT WO 99/18055 publishes Apr. 15, 1999, PCT WO 01/60770 published Aug. 23, 2001 and U.S. patent application Ser. No. 09/627,634 filed Jul. 28, 2000, U.S. patent application Ser. No. 09/507,838 filed Feb. 22, 2000, and U.S. patent application Ser. No. 09/785,409 filed Feb. 16, 2001, which are all herein fully incorporated by reference.

In an embodiment, an integrated process is directed to producing light olefin(s) from a hydrocarbon feedstock, preferably a hydrocarbon gas feedstock, more preferably methane and/or ethane. The first step in the process is passing the gaseous feedstock, preferably in combination with a water stream, to a syngas production zone to produce a synthesis gas (syngas) stream. Syngas production is well known, and typical syngas temperatures are in the range of from about 700° C. to about 1200° C. and syngas pressures are in the range of from about 2 MPa to about 100 MPa. Synthesis gas streams are produced from natural gas, petroleum liquids, and carbonaceous materials such as coal, recycled plastic, municipal waste or any other organic material, preferably synthesis gas stream is produced via steam reforming of natural gas. Generally, a heterogeneous catalyst, typically a copper based catalyst, is contacted with a synthesis gas stream, typically carbon dioxide and carbon monoxide and hydrogen to produce an alcohol, preferably methanol, often in combination with water. In one embodiment, the synthesis gas stream at a synthesis temperature in the range of from about 150° C. to about 450° C. and at a synthesis pressure in the range of from about 5 MPa to about 10 MPa is passed through a carbon oxide conversion zone to produce an oxygenate containing stream.

This oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil. The oxygenate containing stream, crude methanol, in the preferred embodiment is passed through well known purification processes, distillation, separation and fractionation, resulting in a purified oxygenate containing stream, for example, commercial Grade A and AA methanol. The oxygenate containing stream or purified oxygenate containing stream, optionally with one or more diluents, is contacted with one or more molecular sieve catalyst composition described above in any one of the processes described above to produce a variety of prime products, particularly light olefin(s), ethylene and/or propylene. Non-limiting examples of this integrated process is described in EP-B-0 933 345, which is herein fully incorporated by reference. In another more fully integrated process, optionally with the integrated processes described above, olefin(s) produced are directed to, in one embodiment, one or more polymerization processes for producing various polyolefins. See, for example, U.S. patent application Ser. No. 09/615,376 filed Jul. 13, 2000, which is herein fully incorporated by reference.

Polymerization processes include solution, gas phase, slurry phase and a high pressure processes, or a combination thereof. Particularly preferred is a gas phase or a slurry phase polymerization of one or more olefin(s) at least one of which is ethylene or propylene. These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. The polymers produced by the polymerization processes described above include linear low density polyethylene, elastomers, plastomers, high density polyethylene, low density polyethylene, polypropylene and polypropylene copolymers. The propylene based polymers produced by the polymerization processes include atactic polypropylene, isotactic polypropylene, syndiotactic polypropylene, and propylene random, block or impact copolymers.

In preferred embodiment, the integrated process comprises a polymerizing process of one or more olefin(s) in the presence of a polymerization catalyst system in a polymerization reactor to produce one or more polymer products, wherein the one or more olefin(s) having been made by converting an alcohol, particularly methanol, using a molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

Molecular Sieves Catalyst Compositions

Molecular sieves have various chemical, physical, and framework characteristics. Molecular sieves have been well classified by the Structure Commission of the International Zeolite Association according to the rules of the IUPAC Commission on Zeolite Nomenclature. A molecular sieve's "framework-type" describes the connectivity and topology of the tetrahedrally coordinated atoms constituting the framework, and makes an abstraction of the specific properties for those materials. Framework-type zeolite and zeolite-type molecular sieves for which a structure has been established are assigned a three letter code and are described in the Atlas of Zeolite Framework Types, 5th edition, Elsevier, London, England (2001), which is herein fully incorporated by reference.

Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof; the medium pore molecular sieves, AFO, AEL, EUO, HEU, FER, MEL, MFI, MTW, MTT, TON, and substituted forms thereof; and the large pore molecular sieves, EMT, FAU, and substituted forms thereof. Other molecular sieves include ANA, BEA, CFI, CLO, DON, GIS, LTL, MER, MOR, MWW and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM and TON. In one preferred embodiment, the molecular sieve of the invention has an AEI framework-type or a CHA framework-type, or a combination thereof, most preferably a CHA framework-type.

Molecular sieve materials all have 3-dimensional framework structure of corner-sharing TO4 tetrahedra, where T is any tetrahedrally coordinated cation. These molecular sieves are typically described in terms of the size of the ring that defines a pore, where the size is based on the number of T atoms in the ring. Other framework-type characteristics include the arrangement of rings that form a cage, and when present, the dimension of channels, and the spaces between the cages. See van Bekkum, et al., Introduction to Zeolite Science and Practice, Second Completely Revised and Expanded Edition, Volume 137, pages 1–67, Elsevier Science, B. V., Amsterdam, Netherlands (2001).

The small, medium and large pore molecular sieves have from a 4-ring to a 12-ring or greater framework-type. In a preferred embodiment, the zeolitic molecular sieves have 8-, 10- or 12-ring structures or larger and an average pore size in the range of from about 3 Å to 15 Å. In the most preferred embodiment, the molecular sieves of the invention, preferably silicoaluminophosphate molecular sieves, have 8-rings and an average pore size less than about 5 Å, preferably in the range of from 3 Å to about 5 Å, more preferably from 3 Å to about 4.5 Å, and most preferably from 3.5 Å to about 4.2 Å.

Molecular sieves, particularly zeolitic and zeolitic-type molecular sieves, preferably have a molecular framework of one, preferably two or more corner-sharing [TO4] tetrahedral units, more preferably, two or more [SiO4], [AlO4] and/or [PO4] tetrahedral units, and most preferably [SiO4], [AlO4] and [PO4] tetrahedral units. These silicon, aluminum, and phosphorous based molecular sieves and metal containing silicon, aluminum and phosphorous based molecular sieves have been described in detail in numerous publications including for example, U.S. Pat. No. 4,567,029 (MeAPO where Me is Mg, Mn, Zn, or Co), U.S. Pat. No. 4,440,871 (SAPO), European Patent Application EP-A-0 159 624 (ELAPSO where El is As, Be, B, Cr, Co, Ga, Ge, Fe, Li, Mg, Mn, Ti or Zn), U.S. Pat. No. 4,554,143 (FeAPO), U.S. Pat. Nos. 4,822,478, 4,683,217, 4,744,885 (FeAPSO), EP-A-0 158 975 and U.S. Pat. No. 4,935,216 (ZnAPSO, EP-A-0 161 489 (CoAPSO), EP-A-0 158 976 (ELAPO, where EL is Co, Fe, Mg, Mn, Ti or Zn), U.S. Pat. No. 4,310,440 (AlPO4), EP-A-0 158 350 (SENAPSO), U.S. Pat. No. 4,973,460 (LiAPSO), U.S. Pat. No. 4,789,535 (LiAPO), U.S. Pat. No. 4,992,250 (GeAPSO), U.S. Pat. No. 4,888,167 (GeAPO), U.S. Pat. No. 5,057,295 (BAPSO), U.S. Pat. No. 4,738,837 (CrAPSO), U.S. Pat. Nos. 4,759,919, and 4,851,106 (CrAPO), U.S. Pat. Nos. 4,758,419, 4,882,038, 5,434,326 and 5,478,787 (MgAPSO), U.S. Pat. No. 4,554,143 (FeAPO), U.S. Pat. No. 4,894,213 (AsAPSO), U.S. Pat. No. 4,913,888 (AsAPO), U.S. Pat. Nos. 4,686,092, 4,846,956 and 4,793,833 (MnAPSO), U.S. Pat. Nos. 5,345,011 and 6,156,931 (MnAPO), U.S. Pat. No. 4,737,353 (BeAPSO), U.S. Pat. No. 4,940,570 (BeAPO), U.S. Pat. Nos. 4,801,309, 4,684,617 and 4,880,520 (TiAPSO), U.S. Pat. Nos. 4,500, 651, 4,551,236 and 4,605,492 (TiAPO), U.S. Pat. Nos. 4,824,554, 4,744,970 (CoAPSO), U.S. Pat. No. 4,735,806 (GaAPSO) EP-A-0 293 937 (QAPSO, where Q is framework oxide unit [QO2]), as well as U.S. Pat. Nos. 4,567,029, 4,686,093, 4,781,814, 4,793,984, 4,801,364, 4,853,197, 4,917,876, 4,952,384, 4,956,164, 4,956,165, 4,973,785, 5,241,093, 5,493,066 and 5,675,050, all of which are fully incorporated herein by reference. Other molecular sieves are described in R. Szostak, Handbook of Molecular Sieves, Van Nostrand Reinhold, New York, N.Y. (1992), which is fully incorporated herein by reference.

The more preferred silicon, aluminum and/or phosphorous containing molecular sieves, and aluminum, phosphorous, and optionally silicon, containing molecular sieves include aluminophosphate (ALPO) molecular sieves and silicoaluminophosphate (SAPO) molecular sieves and substituted, preferably metal substituted, ALPO and SAPO molecular sieves. The most preferred molecular sieves are SAPO molecular sieves, and metal substituted SAPO molecular sieves. In an embodiment, the metal is an alkali metal of Group IA of the Periodic Table of Elements, an alkaline earth metal of Group IIA of the Periodic Table of Elements, a rare earth metal of Group IIIB, including the Lanthanides: lanthanum, cerium, praseodymium, neodymium, samarium, europium, gadolinium, terbium, dysprosium, holmium, erbium, thulium, ytterbium and lutetium; and scandium or yttrium of the Periodic Table of Elements, a transition metal of Groups IVB, VB, VIIB, VIIB, VIIIB, and IB of the Periodic Table of Elements, or mixtures of any of these metal species. In one preferred embodiment, the metal is selected from the group consisting of Co, Cr, Cu, Fe, Ga, Ge, Mg, Mn, Ni, Sn, Ti, Zn and Zr, and mixtures thereof. In another preferred embodiment, these metal atoms discussed above are inserted into the framework of a molecular sieve through a tetrahedral unit, such as [MeO2], and carry a net charge depending on the valence state of the metal substituent. For example, in one embodiment, when the metal substituent has a valence state of +2, +3, +4, +5, or +6, the net charge of the tetrahedral unit is between −2 and +2.

In one embodiment, the molecular sieve, as described in many of the U.S. patents mentioned above, is represented by the empirical formula, on an anhydrous basis:

$$mR:(M_xAl_yP_z)O_2$$

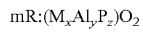

wherein R represents at least one templating agent, preferably an organic templating agent; m is the number of moles of R per mole of $(M_xAl_yP_z)O_2$ and m has a value from 0 to 1, preferably 0 to 0.5, and most preferably from 0 to 0.3; x, y, and z represent the mole fraction of M, Al and P as tetrahedral oxides, where M is a metal selected from one of Group IA, IIA, IB, IIIB, IVB, VB, VIIB, VIIB, VIIIB and Lanthanide's of the Periodic Table of Elements, preferably M is selected from one of the group consisting of Co, Cr, Cu, Fe, Ga, Ge, Mg, Mn, Ni, Sn, Ti, Zn and Zr. In an embodiment, m is greater than or equal to 0.2, and x, y and z are greater than or equal to 0.01. In another embodiment, m is greater than 0.1 to about 1, x is greater than 0 to about 0.25, y is in the range of from 0.4 to 0.5, and z is in the range of from 0.25 to 0.5, more preferably m is from 0.15 to 0.7, x is from 0.01 to 0.2, y is from 0.4 to 0.5, and z is from 0.3 to 0.5.

Non-limiting examples of SAPO and ALPO molecular sieves of the invention include one or a combination of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44 (U.S. Pat. No. 6,162,415), SAPO-47, SAPO-56, ALPO-5, ALPO-11, ALPO-18, ALPO-31, ALPO-34, ALPO-36, ALPO-37, ALPO-46, and metal containing molecular sieves thereof.

Preferably, the molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. The more preferred zeolite-type molecular sieves include one or a combination of SAPO-18, SAPO-34, SAPO-35, SAPO-44, SAPO-56, ALPO-18 and ALPO-34, even more preferably one or a combination of SAPO-18, SAPO-34, ALPO-34 and ALPO-18, and metal containing molecular sieves thereof, and most preferably one or a combination of SAPO-34 and ALPO-18, and metal containing molecular sieves thereof. Optionally, the molecular sieve is selected from the group consisting of SAPO-34, the metal containing forms thereof, and mixtures thereof.

The catalyst particles that is directed to the size-selective separation unit according to the present invention optionally contain molecular sieves selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

In an embodiment, the molecular sieve is an intergrowth material having two or more distinct phases of crystalline structures within one molecular sieve composition. In particular, intergrowth molecular sieves are described in the U.S. patent application Ser. No. 09/924,016 filed Aug. 7, 2001 and PCT WO 98/15496 published Apr. 16, 1998, both of which are herein fully incorporated by reference. For example, SAPO-18, ALPO-18 and RUW-18 have an AEI framework-type, and SAPO-34 has a CHA framework-type. In another embodiment, the molecular sieve comprises at least one intergrown phase of AEI and CHA framework-types, preferably the molecular sieve has a greater amount of CHA framework-type to AEI framework-type, and more preferably the molar ratio of CHA to AEI is greater than 1:1.

In one embodiment, the attrition resistance of a molecular sieve catalyst composition is measured using an Attrition Rate Index (ARI), measured in weight percent catalyst composition attrited per hour. ARI is measured by adding 6.0 g of catalyst composition having a particles size ranging from 53 microns to 125 microns to a hardened steel attrition cup. Approximately 23,700 cc/min of nitrogen gas is bubbled through a water-containing bubbler to humidify the nitrogen. The wet nitrogen passes through the attrition cup, and exits the attrition apparatus through a porous fiber thimble. The flowing nitrogen removes the finer particles, with the larger particles being retained in the cup. The porous fiber thimble separates the fine catalyst particles from the nitrogen that exits through the thimble. The fine particles remaining in the thimble represent the catalyst composition that has broken apart through attrition. The nitrogen flow passing through the attrition cup is maintained for 1 hour. The fines collected in the thimble are removed from the unit. A new thimble is then installed. The catalyst left in the attrition unit is attrited for an additional 3 hours, under the same gas flow and moisture levels. The fines collected in the thimble are recovered. The collection of fine catalyst particles separated by the thimble after the first hour are weighed. The amount in grams of fine particles divided by the original amount of catalyst charged to the attrition cup expressed on per hour basis is the ARI, in weight percent per hour (wt. %/hr). ARI is represented by the formula: ARI=C/(B+C)/D multiplied by 100%, wherein B is weight of catalyst composition left in the cup after the attrition test, C is the weight of collected fine catalyst particles after the first hour of attrition treatment, and D is the duration of treatment in hours after the first hour attrition treatment.

In one embodiment, the molecular sieve catalyst composition or formulated molecular sieve catalyst composition has an ARI less than 15 weight percent per hour, preferably less than 10 weight percent per hour, more preferably less than 5 weight percent per hour, and even more preferably less than 2 weight percent per hour, and most preferably less than 1 weight percent per hour. In one embodiment, the molecular sieve catalyst composition or formulated molecular sieve catalyst composition has an ARI in the range of from 0 weight percent per hour to less than 5 weight percent per hour, more preferably from about 0.05 weight percent per hour to less than 3 weight percent per hour, and most preferably from about 0.01 weight percent per hour to less than 2 weight percent per hour.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

The invention claimed is:

1. A process for selectively removing large catalyst particles from a reaction system, wherein the reaction system comprises a reaction zone and a disengaging zone, the process comprising the steps of:
   (a) feeding a plurality of catalyst particles into the reaction zone, wherein the plurality of catalyst particles comprises a molecular sieve selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof;
   (b) contacting the plurality of catalyst particles with a feedstock comprising an oxygenate in the reaction zone under conditions effective to convert at least a portion of the feedstock to product comprising light olefins;
   (c) separating a portion of the catalyst particles from the product in a disengaging zone;
   (d) directing a portion of the plurality of catalyst particles separated in the disengaging zone to a counter-flow cyclone separator, wherein the portion of the plurality of catalyst particles has a first median particle diameter;
   (e) separating the portion of the plurality of catalyst particles in the counter-flow cyclone separator into a small catalyst stream and a large catalyst stream by modulating flow rate of a gas stream to the cyclone separator to control particle size of the catalyst streams, wherein the small catalyst stream has a second median particle diameter less than the first median particle diameter; and
   (f) directing at least a portion of the small catalyst stream to the reaction system.

2. A process for selectively removing large catalyst particles from a reaction system, wherein the reaction system comprises a reaction zone, and a disengaging zone, the process comprising the steps of:
   (a) feeding a plurality of catalyst particles into the reaction zone;
   (b) contacting the plurality of catalyst particles with a feedstock in the reaction zone under conditions effective to convert at least a portion of the feedstock to product and to at least partially deactivate at least a portion of the catalyst particles;
   (c) separating a portion of the catalyst particles from the product in a disengaging zone;
   (d) regenerating at least a portion of the partially deactivated catalyst in a catalyst regenerator to form regenerated catalyst particles;
   (e) directing the at least a portion of the regenerated catalyst particles from the catalyst regenerator to a counter-flow cyclone separator, wherein the portion of the regenerated catalyst particles has a first median particle diameter;
   (f) separating the regenerated catalyst particles in the counter-flow cyclone separator into a small catalyst stream and a large catalyst stream by modulating flow rate of a gas stream to the cyclone separator to control particle size of the catalyst streams, wherein the small catalyst stream has a second median particle diameter less than the first median particle diameter; and
   (g) directing at least a portion of the small catalyst stream to the reaction system.

3. A process for selectively removing large catalyst particles from a reaction system, wherein the reaction system comprises a reaction zone, and a disengaging zone, the process comprising the steps of:
   (a) feeding a plurality of catalyst particles into the reaction zone;
   (b) contacting the plurality of catalyst particles with a feedstock in the reaction zone under conditions effective to convert at least a portion of the feedstock to product and to at least partially deactivate at least a portion of the catalyst particles;
   (c) separating a portion of the catalyst particles from the product in a disengaging zone;
   (d) stripping at least a portion of the partially deactivated catalyst in a catalyst stripper to form stripped catalyst particles;
   (e) directing the at least a portion of the stripped catalyst particles from the catalyst stripper to counter-flow cyclone separator, wherein the portion of the stripped catalyst particles has a first median particle diameter;
   (f) separating the stripped catalyst particles in the counter-flow cyclone separator into a small catalyst stream and a large catalyst stream by modulating flow rate of a gas stream to the cyclone separator to control particle size of the catalyst streams, wherein the small catalyst stream has a second median particle diameter less than the first median particle diameter; and
   (g) directing at least a portion of the small catalyst stream to the reaction system.

4. A process for selectively removing large catalyst particles from a reaction system, wherein the reaction system comprises a reaction zone, and a disengaging zone, the process comprising the steps of:
   (a) feeding a plurality of catalyst particles into the reaction zone;
   (b) contacting the plurality of catalyst particles with a feedstock in the reaction zone under conditions effective to convert at least a portion of the feedstock to product;
   (c) separating a portion of the catalyst particles from the product in a disengaging zone;
   (d) removing at least a portion of the separated catalyst particles from the disengaging zone;
   (e) cooling at least a portion of the particles removed from the disengaging zone in a catalyst cooler, (f) directing at least a portion of the cooled catalyst particles from the catalyst cooler to counter-flow cyclone separator, wherein the portion of the stripped catalyst particles has a first median particle diameter;

(g) separating the cooled catalyst particles in the counter-flow cyclone separator into a small catalyst stream and a large catalyst stream by modulating flow rate of a gas stream to the cyclone separator to control particle size of the catalyst streams, wherein the small catalyst stream has a second median particle diameter less than the first median particle diameter; and (h) directing at least a portion of the small catalyst stream to the reaction system.

5. A reaction process in which catalyst particles are separated according to median particle size and directed to a reaction zone, the process comprising the steps of:

a) contacting catalyst particles with a feedstock in the reaction zone to convert at least a portion of the feedstock to product;

b) separating a portion of the catalyst particles from the product;

c) directing at least a portion of the separated catalyst particles to a separation unit;

d) modulating flow rate of a gas stream to the separation unit to separate catalyst particles in the separation unit into a first catalyst stream having a median particle diameter smaller than that of a second catalyst stream;

e) directing at least a portion of the first catalyst stream to the reaction zone, and f) monitoring the median particle diameter of the first catalyst stream.

6. The process of claim 5, wherein the monitoring is performed by a laser scattering particle size analyzer, a Coulter counter, a device for determining rate of sedimentation, or a mechanical screening device.

7. The reaction process of claim 5, wherein the catalyst particles are separated from the product in a disengaging zone having a larger cross sectional area than that of the reaction zone.

8. The reaction process of claim 5, wherein the separation unit is selected from the group consisting of: a cyclone separator, a settling vessel, a screen, and an air classifier.

9. The reaction process of claim 5, wherein the separation unit comprises a counter-flow cyclone separator.

10. The reaction process of claim 5, wherein the feedstock comprises an oxygenate and the product comprises light olefins.

11. The reaction process of claim 5, wherein the first catalyst stream has a median particle diameter greater than 20 microns and less than 120 microns.

12. A reaction process in which catalyst articles are separated according to median article size and directed to a reaction zone, the process comprising the steps of:

a) contacting catalyst particles with a feedstock in the reaction zone to convert at least a portion of the feedstock to product and form an at least partially deactivated catalyst;

b) separating a portion of the partially deactivated catalyst particles from the product;

c) regenerating at least a portion of the partially deactivated catalyst in a catalyst regenerator and directing at least a portion of the regenerated catalyst from the catalyst regenerator to a separation unit;

d) modulating flow rate of a gas stream to the separation unit to separate catalyst particles in the separation unit into a first catalyst stream having a median particle diameter smaller than that of a second catalyst stream; and e) directing at least a portion of the first catalyst stream to the reaction zone.

13. A reaction process in which catalyst particles are separated according to median particle size and directed to a reaction zone, the process comprising the steps of:

a) contacting catalyst particles with a feedstock in the reaction zone to convert at least a portion of the feedstock to product and form an at least partially deactivated catalyst;

b) separating a portion of the partially deactivated catalyst particles from the product;

c) stripping at least a portion of the partially deactivated catalyst in a catalyst stripper and directing at least a portion of the stripped catalyst from the catalyst stripper to a separation unit;

d) modulating flow rate of a gas stream to the separation unit to separate catalyst particles in the separation unit into a first catalyst stream having a median particle diameter smaller than that of a second catalyst stream; and e) directing at least a portion of the first catalyst stream to the reaction zone.

14. A reaction process in which catalyst particles are separated according to median particle size and directed to a reaction zone, the process comprising the steps of:

a) contacting catalyst particles with a feedstock in the reaction zone to convert at least a portion of the feedstock to product;

b) separating a portion of the catalyst particles from the product;

c) cooling heated catalyst separated from the product in the reaction system in a catalyst cooler;

d) directing at least a portion of the cooled catalyst from the catalyst cooler to a separation unit;

e) modulating flow rate of a gas stream to the separation unit to separate catalyst particles in the separation unit into a first catalyst stream having a median particle diameter smaller than that of a second catalyst stream; and f) directing at least a portion of the first catalyst stream to the reaction zone.

* * * * *